(12) United States Patent
Lykke Sørensen et al.

(10) Patent No.: US 11,993,649 B2
(45) Date of Patent: May 28, 2024

(54) ANTIBODIES AGAINST MFAP4

(71) Applicant: SYDDANSK UNIVERSITET, Odense M (DK)

(72) Inventors: Grith Lykke Sørensen, Odense S (DK); Anders Schlosser, Odense SV (DK); Uffe Holmskov, Odense S (DK)

(73) Assignee: SYDDANSK UNIVERSITET, Odense M (DK)

(*) Notice: Subject to any disclaimer, the term of this patent is extended or adjusted under 35 U.S.C. 154(b) by 764 days.

(21) Appl. No.: 16/760,490

(22) PCT Filed: Nov. 1, 2018

(86) PCT No.: PCT/EP2018/079949
§ 371 (c)(1),
(2) Date: Apr. 30, 2020

(87) PCT Pub. No.: WO2019/086580
PCT Pub. Date: May 9, 2019

(65) Prior Publication Data
US 2023/0047179 A1    Feb. 16, 2023

(30) Foreign Application Priority Data
Nov. 1, 2017    (EP) ..................... 17199552

(51) Int. Cl.
*C07K 16/28*    (2006.01)
*A61K 39/00*    (2006.01)

(52) U.S. Cl.
CPC ........ *C07K 16/28* (2013.01); *A61K 2039/505* (2013.01); *C07K 2317/56* (2013.01); *C07K 2317/73* (2013.01); *C07K 2317/76* (2013.01)

(58) Field of Classification Search
CPC ............... C07K 16/28; C07K 2317/56; C07K 2317/73; C07K 2317/76; C07K 16/18; A61K 2039/505
USPC ...................................... 424/133.1
See application file for complete search history.

(56) References Cited

U.S. PATENT DOCUMENTS

2015/0361165 A1* 12/2015 Sorensen ............... C07K 16/18
                                                530/389.1

FOREIGN PATENT DOCUMENTS

| WO | 2009103157 A1 | 8/2009 |
| WO | 2014114298 A1 | 7/2014 |
| WO | 2016008498 A1 | 1/2016 |

OTHER PUBLICATIONS

Rudikoff et al (Proc. Natl. Acad. Sci. USA, 79(6):1979-1983, Mar. 1982).*
Colman P. M. (Research in Immunology, 145:33-36, 1994).*
Köhler et al., "Continuous cultures of fused cells secreting antibody of predefined specificity" The Journal of Immunology, Nature, 256 (5517) 495-497 (1975).
Smith et al., "Identification of Common Molecular Subsequences", J. Mol. Biol. (1981), 147, 195-197.
Rognes "ParAlign: a parallel sequence alignment algorithm for rapid and sensitive database searches", Nucleic Acids Research, 2001, vol. 29, No. 7, 1647-1652.
Lausen et al., "Microfibril-associated Protein 4 Is Present in Lung Washings and Binds to the Collagen Region of Lung Surfactant Protein D" J. Biol. Chem., Issue of Nov. 5, 274(45), 1999, pp. 32234-32240.
Pilecki, et al., "Microfibrillar-associated protein 4 deficiency attenuates experimental allergic airway inflammation", Immunol. Conference Abstract: 15th International Congress of Immunology, Aug. 22, 2013, 2 pages.
Wulf-Johansson et al., "Localization of Microfibrillar-Associated Protein 4 (MFAP4) in Human Tissues: Clinical Evaluation of Serum MFAP4 and Its Association with Various Cardiovascular Conditions", Plos One, vol. 8, No. 12, Dec. 13, 2013, e82243, 11 pages.
Kabsch, "Integration, scaling, space-group assignment and post-refinement" Acta Crystallographica Section D, Biological crystallography 66, (2010) pp. 133-144.
McCoy, et al., "Phaser crystallographic software", Journal of Applied Crystallography 40, (2007) pp. 658-674.
Afonine, et al., "Towards automated crystallographic structure refinement with phenix.refine" Acta Crystallographica Section D, Acta Cryst. D68, (2012) pp. 352-367.
Croll, et al., "Re-evaluation of low-resolution crystal structures via interactive molecular-dynamics flexible fitting (iMDFF): a case study in complement C4" Acta Cryst D, Structural Biology, D72, (2016), pp. 1006-1016.
Shrive, et al., "Crystal Structure of the Tetrameric Fibrinogen-like Recognition Domain of Fibrinogen C Domain Containing 1 (FIBCD1) Protein" The Journal of Biological Chemistry vol. 289, No. 5, pp. 2880-2887, Jan. 31, 2014.
Chen, et al., "MolProbity: all-atom structure validation for macromolecular crystallography" Acta Crystallographica Section D, Biol Crystallogr. D66, (2010) pp. 12-21.
Krissinel, et al., "Inference of Macromolecular Assemblies from Crystalline State" J. Mol. Biol. (2007) 372, pp. 774-797.
International Search Report and Written Opinion issued in PCT/EP2018/079949, dated Jan. 23, 2019.
International Preliminary Report on Patentability and Written Opinion issued in PCT/EP2018/079949, dated May 14, 2020.

* cited by examiner

*Primary Examiner* — Yan Xiao
(74) *Attorney, Agent, or Firm* — BakerHostetler

(57) ABSTRACT

The present invention relates to antibodies, including humanized antibodies that bind human Microfibrillar-associated protein 4 (MFAP4). The invention also relates to uses of such antibodies.

17 Claims, 12 Drawing Sheets
Specification includes a Sequence Listing.

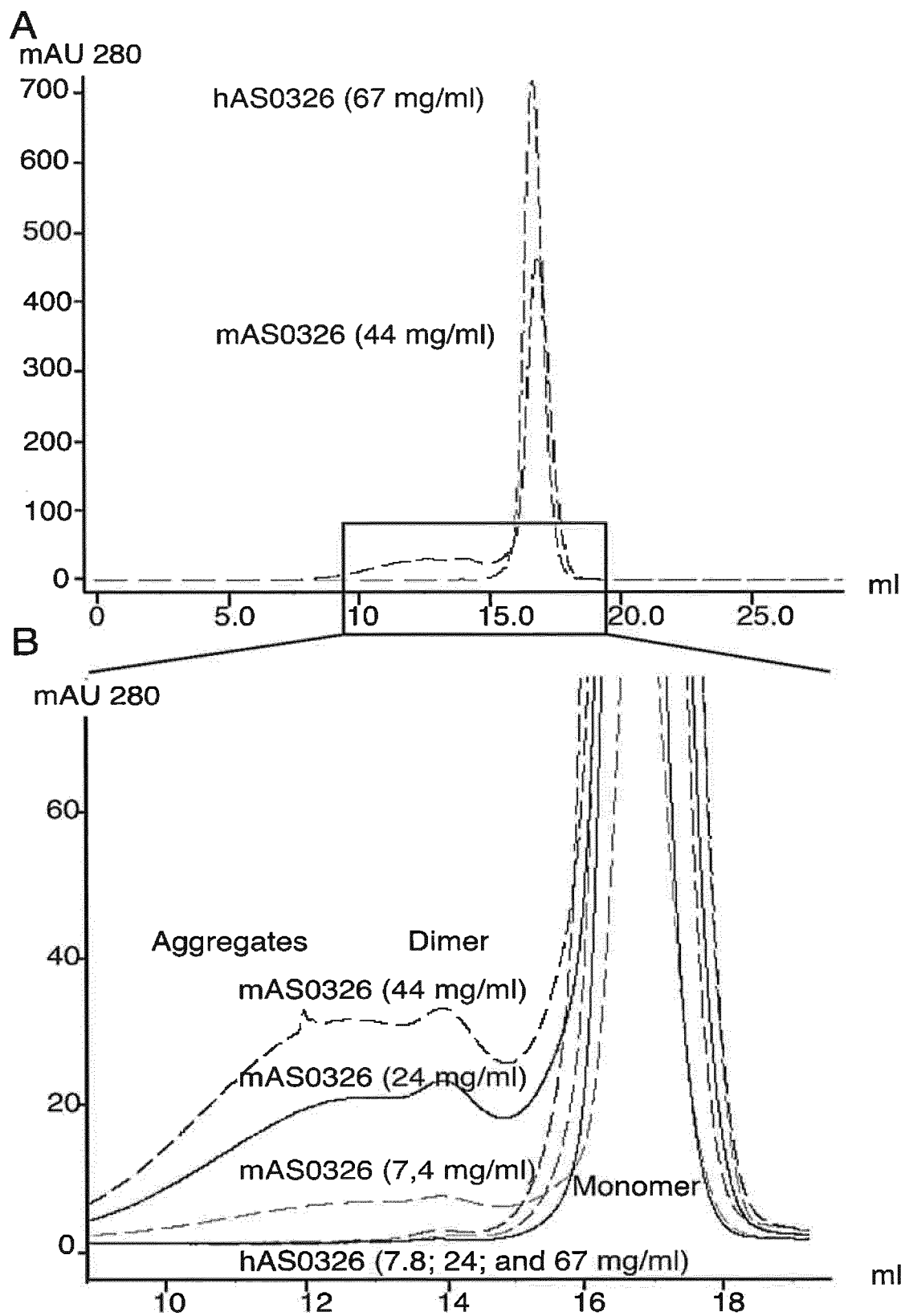
Fig. 5A-B

ANTIBODIES AGAINST MFAP4

CROSS-REFERENCE TO RELATED APPLICATIONS

This application is a 35 U.S.C. § 371 national phase application of International Patent Application No. PCT/EP2018/079949, filed Nov. 1, 2018, which claims priority to EP Patent Application No. 17199552.5, filed Nov. 1, 2017, the entire disclosures of each of which are incorporated herein by reference in their entirety.

SEQUENCE LISTING

The instant application contains a sequence listing which has been submitted electronically in ASCII format and is hereby incorporated by reference in its entirety. The ASCII copy, created on Oct. 25, 2021, is named 118467.000002_SL.txt and is 10.3 KB in size.

TECHNICAL FIELD OF THE INVENTION

The invention relates generally to medicine and the use of antibodies. The present invention specifically relates to a novel antibody, in particular a humanized monoclonal antibody that binds human Microfibrillar-associated protein 4 (MFAP4).

BACKGROUND OF THE INVENTION

MFAP4 is a 36 kDa glycoprotein composed of a short N-terminal region that contains a potential integrin binding RGD sequence followed by a fibrinogen related domain (FReD). The protein forms a homo-oligomeric structure under native conditions. FReDs are found in a diverse group of human proteins involved in different functions such as coagulation, angiogenesis, tissue growth and remodeling, and innate immunity.

MAGP-36/MFAP4 was first identified as a protein with tenascin resemblance in the amino acid composition and localized to ECM in arteries. MAGP-36 was following demonstrated with direct interaction with ECM fibres including elastin, collagen, or calvasculin. The interaction between MAGP-36 and cellular integrin receptors was demonstrated using inhibition by RGD containing peptides of human aortic smooth muscle cells in attachment to immobilized MAGP-36.

WO 2014/114298 discloses different antibodies (including HG-HYB 7-5), which target MFAP4.

WO 2016/008498 also discloses antibodies, which target MFAP4 (including HG-HYB 7-1).

Hence, improved antibodies against MFAP4 would be advantageous, and in particular a more efficient and/or reliable antibody, which binds to MFAP4 would be advantageous. In addition, new uses of MFAP4 antibodies would be advantageous.

SUMMARY OF THE INVENTION

The present invention provides novel antibodies targeting MFAP4, including humanized antibodies. These antibodies have different sequences and different binding properties compared to known antibodies targeting MFAP4.

All RGD dependent integrins may potentially interact with this RGD site, however integrins $\alpha V\beta 3/5$ are highly relevant for investigation of vascular remodelling, angiogenesis, vascular leakage and inflammation.

Medical uses of the antibodies according to the invention are described in the example section.

Thus, an object of the present invention relates to the provision of novel ligands (antibodies) targeting MFAP4. In particular, it is an object of the present invention to provide humanized antibodies against MFAP4.

Thus, one aspect of the invention relates to a protein ligand, such as an antibody, which binds to a new epitope of MFAP4.

Another aspect of the present invention relates to a protein ligand, such as an antibody, or the ligand according to the invention, comprising
  a light chain variable region comprising a CDR 1 region according SEQ ID NO: 9, a CDR 2 region according to SEQ ID NO: 10 and a CDR 3 region according to SEQ ID NO: 11; and
  a heavy chain variable region comprising a CDR 1 region according SEQ ID NO: 12, a CDR 2 region according to SEQ ID NO: 13 and a CDR 3 region according to SEQ ID NO: 14.

Yet another aspect of the present invention is to provide a protein ligand, such as an antibody, or the ligand according to the invention, comprising
  a light chain variable region comprising the amino acid sequence of SEQ ID NO: 1 or 3, or sequences having at least 80% sequence identity, such as at least 90% sequence identity, or such as at least 95% sequence identity to SEQ ID NO: 1 or 3.
  a heavy chain variable region comprising the amino acid sequence of SEQ ID NO: 2 or 4, or sequences having at least 80% sequence identity, such as at least 90% sequence identity, or such as at least 95% sequence identity to SEQ ID NO: 2 or 4.

Still another aspect of the present invention is to provide a vector encoding the ligand according to the invention.

A further aspect relates to a cell expressing the ligand according to the invention, and/or a cell comprising the vector according to the invention.

Yet a further aspect relates to a composition comprising the ligand according to the invention, and one or more physiologically acceptable carriers, excipients and/or diluents.

An additional aspect relates to ligand according to the invention and/or composition according to the invention, for use as a medicament.

Yet an aspect relates to the ligand according to the invention or the composition according to the invention for use in the prevention or treatment of vascular diseases characterized by pathological proliferation or vascular leakage or inflammation or fibrosis and/or related disorders in a mammal.

(HYB7-18), HG HYB 7-5 (HYB7-5), hAS0326 and mAS0326 in a 2-fold dilution from 20 µg/ml. The resulting binding patterns demonstrate that the binding of biotinylated monoclonal antibody of interest to immobilized target recombinant MFAP4 can be inhibited by the same unlabelled Mab. Only HG Hyb 7-5 was capable of inhibiting the HG HYB 7-5 interaction with target. In contrast, mAS0326 was capable of inhibiting hAS0326 binding to target and vice versa.

Figure 3:
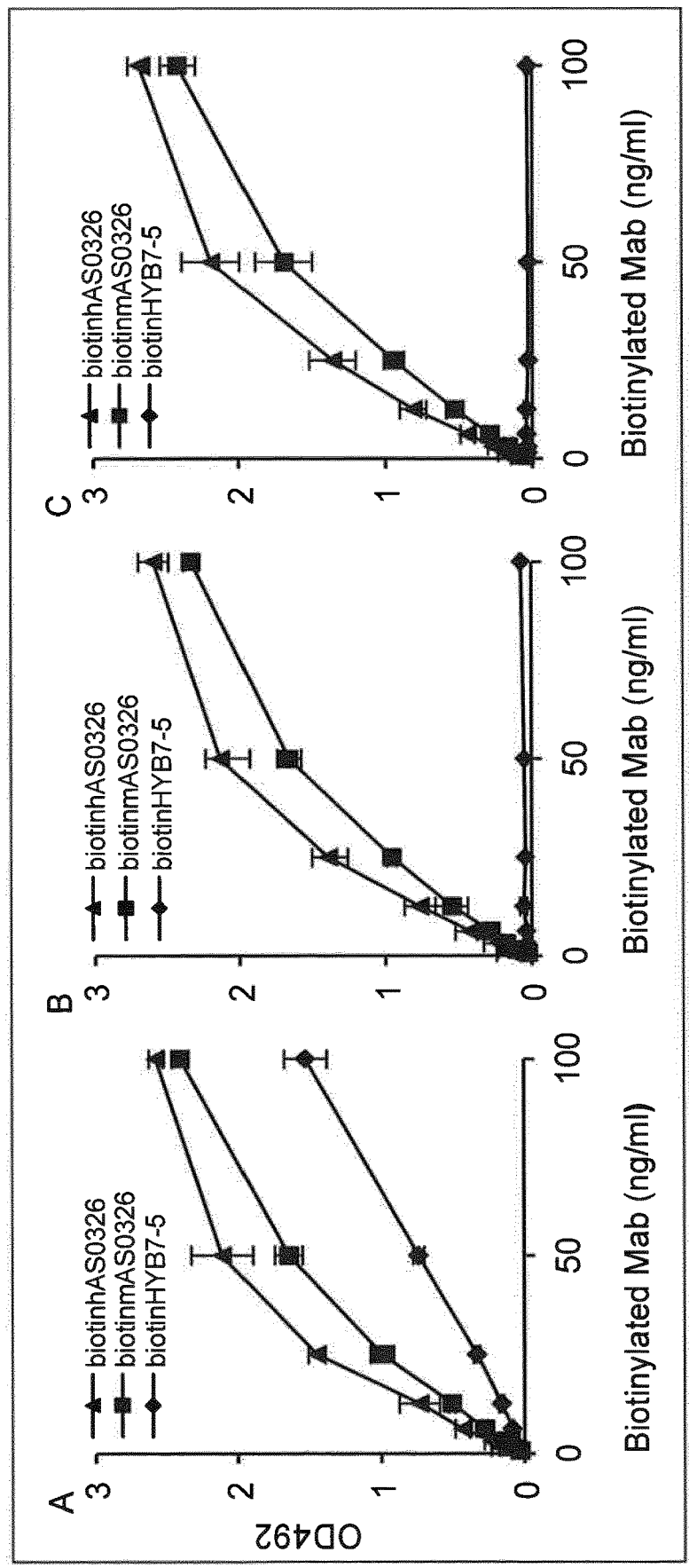

FIG. 3 shows binding of biotinylated monoclonal antibodies (Mab) hAS0326 (biotinhAS0326), mAS0326 (biotinmAS0326) and HG HYB 7-5 (biotinHYB7-5) to A) recombinant human MFAP4, B) recombinant human MFAP4 with RGD integrin binding motif mutated to AAA and C) recombinant mouse MFAP4.

Figure 4:
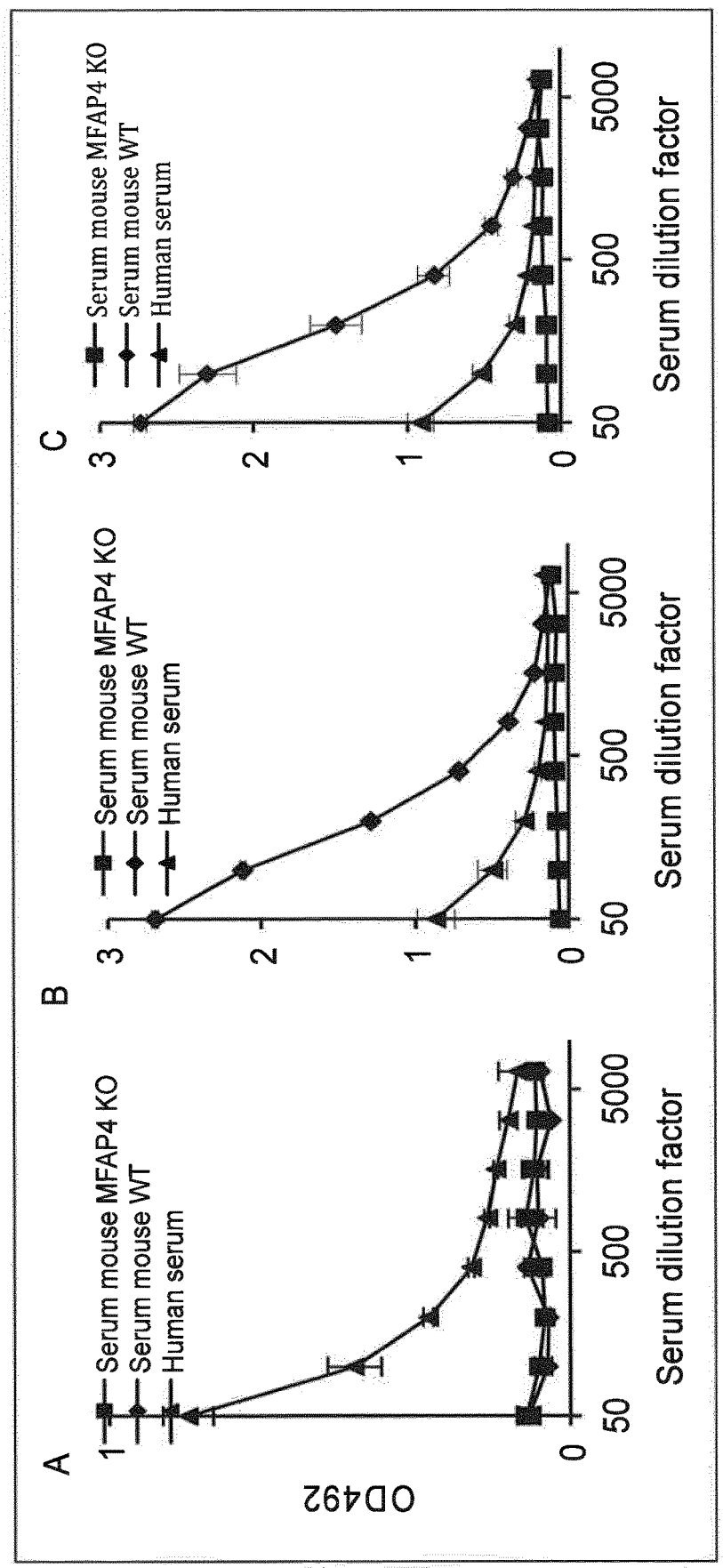

FIG. 4 shows binding of HG HYB 7-5, mAS0326 and hAS0326 to mouse serum MFAP4 and human serum MFAP4. Serum from MFAP4-deficient mice (MFAP4 KO) is included as negative control. Microtiter plates coated with A) HG HYB 7-5, B) mAS0326 and C) hAS0326. Biotinylated HG HYB 7-18 was used as detector antibody.

Figure 5C:
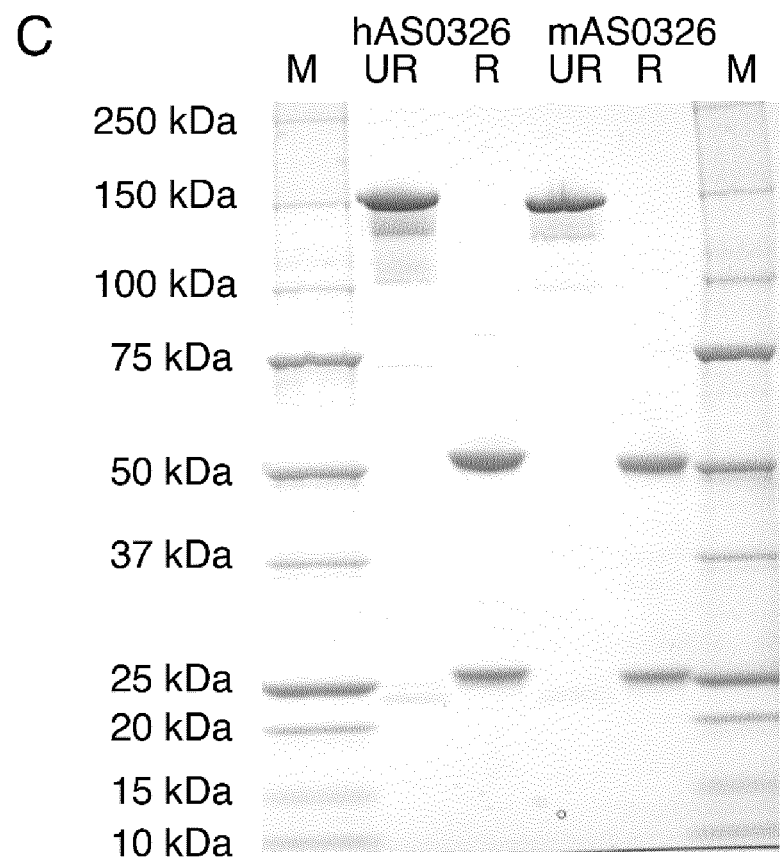

FIG. 5 shows antibody aggregation in solution. hAS0326 and mAS0326 were concentrated to the indicated concentrations [7.4 mg/ml-67 mg/ml] before size exclusion chromatography (SEC) was performed. A) SEC chromatogram with mAS0326 concentrated to 44 mg/ml and hAS0326 concentrated to 67 mg/ml. B) Zoom of the SEC chromatogram for all tested concentrations. C) Test of purity using SDS-PAGE and Commassie staining of 3 µg/lane of hAS0326 and mAS0326 in the reduced state (R) and unreduced state (UR) (M=MW marker).

FIG. 6 shows mAS0326-mediated inhibition of pathological ocular angiogenesis, vascular leakage and inflammatory infiltration in the mouse laser-induced CNV model. Intraocular injections of antibodies were performed on day 1 and day 7 after laser burn. There are 4-8 mice per treatment group with up to 4 lesions per eye. Each data point represents one lesion. Fundus fluorescein angiography at A) day 7 and B) day 14 shows a decrease in lesion size (combined angiogenesis/vascular leakage) in eyes treated with either mAS0326 or anti-VEGF. Scale bar=100 µm. Intraocular injection of mAS0326 also reduces angiogenesis per se (as measured by endothelial marker Lectin IB4 positive volume of the choroid) C) and CD45 (inflammatory cell) positive cells infiltrating the choroids D). Scale bar=50 µm. Data in C and D are obtained by confocal imaging of excised choroidal tissue 14 days after laser induced choroidal neovascularization. Statistics shown are for comparison between treatment groups only (scatterplots with median and interquartile range). * $p<0.05$, *** $p<0.001$ (Kruskall-Wallis test and Dunn's multiple comparisons test).

FIG. 7 shows hAS0326-mediated inhibition of pathological ocular angiogenesis, vascular leakage and inflammatory infiltration in the mouse laser-induced CNV model.

Intraocular injections of antibodies were performed on day 1 and day 7 after laser burn. There are 6-8 mice per treatment group with up to 4 lesions per eye. Each data point represents one lesion. Fundus fluorescein angiography at A) day 7 and B) day 14 shows a decrease in lesion size (combined angiogenesis/vascular leakage) in eyes treated with hAS0326 compared to anti-VEGF treated eyes. Intraocular injection of hAS0326 also reduces angiogenesis per se (as measured by endothelial marker Lectin IB4 positive volume of the choroid) C) and CD45 (inflammatory cell) positive cells infiltrating the choroids. The combinatorial treatment with hAS0326 and anti-VEGF enhances this effect further D). Data in C and D are obtained by confocal imaging of excised choroidal tissue 14 days after laser induced choroidal neovascularization. Statistics shown are for comparison between treatment groups only (scatterplots with median and interquartile range). * $p<0.05$,  $p<0.01$, * $p<0.001$, **** $p<0.0001$ (Kruskall-Wallis test and Dunn's multiple comparisons test). Scale bar=100 µm.

Figure 8:
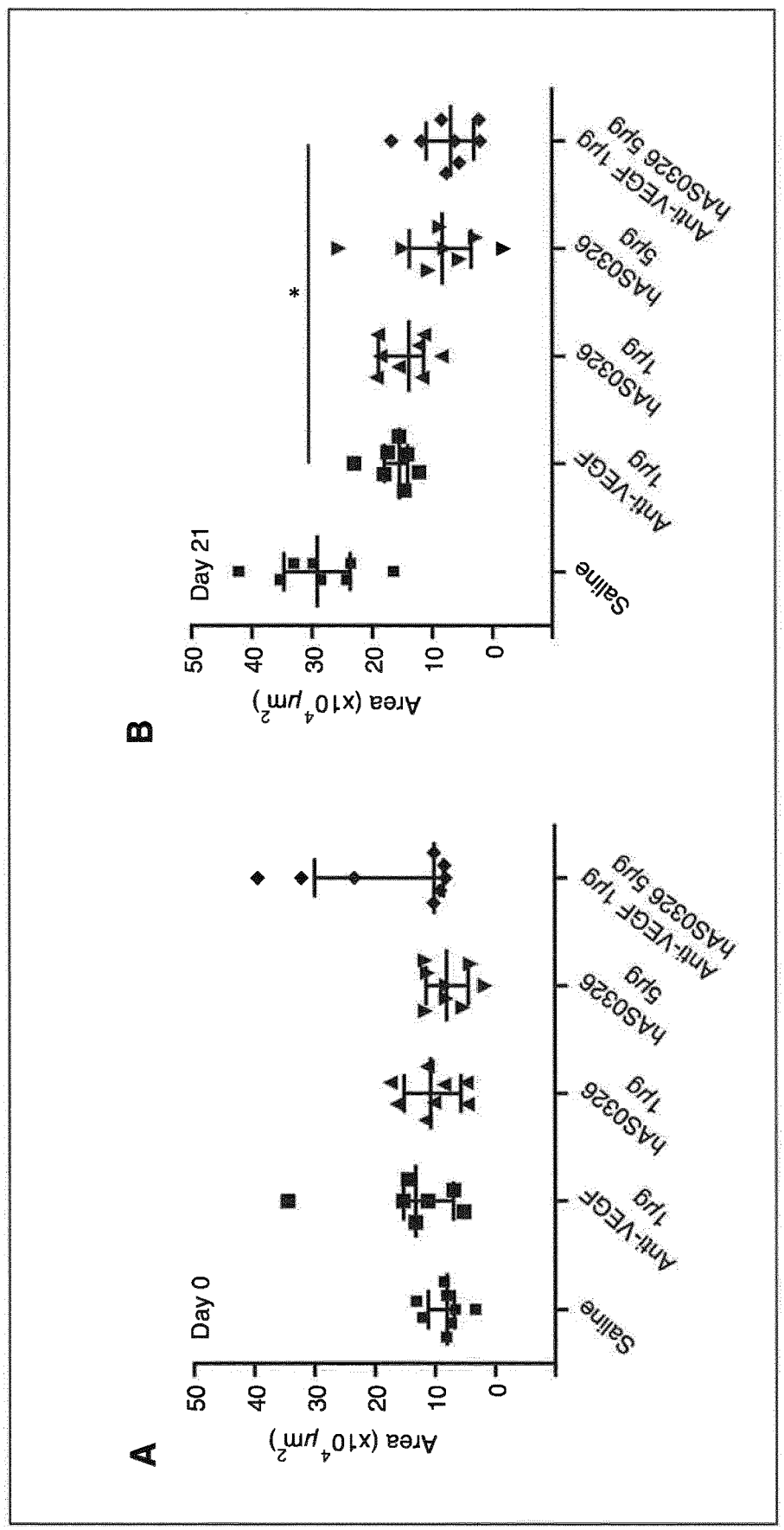

FIG. 8 shows hAS0326-mediated inhibition of pathological ocular leakage in streptozotozin (STZ)-induced rat diabetes model. STZ (50 mg/kg, i.p.) was used to induce diabetes in Sprague-Dawley rats (n=8). Diabetic rats were treated with intraocular injections of antibodies on day 1 and day 7 after onset of STZ treatment. Vascular area was calculated as the mean from three parts of the retina in each animal using Imaris software and measured as area occupied by Evans Blue dye positive vasculature in a 2D plane. Statistics shown are for comparison between treatment groups only (scatterplots with median and interquartile range). * $p<0.05$ (Kruskall-Wallis test and Dunn's multiple comparisons test). A) Day 0; B) Day 21.

Figure 9:
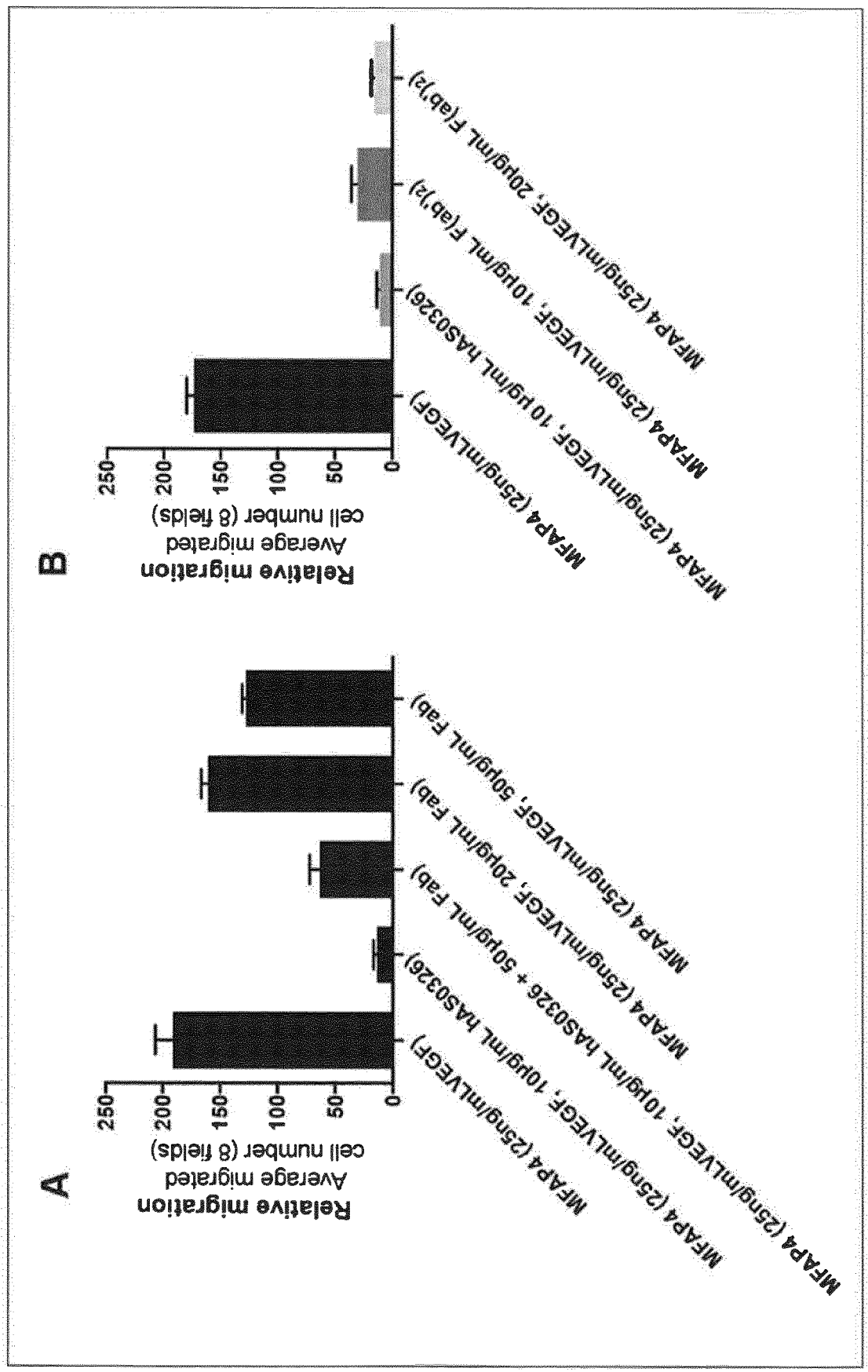

FIG. 9 shows the ability of hAS0326 and variants thereof to inhibit MFAP4-induced cellular activation as assessed by retinal endothelial migration assay. Retinal endothelial migration towards VEGF was assayed using transwell filters. A) Full-length hAS0326- versus Fab-mediated inhibition of endothelial migration and B) Full-length hAS0326- versus F(ab')$_2$-mediated inhibition of endothelial migration.

The present invention will now be described in more detail in the following.

DETAILED DESCRIPTION OF THE INVENTION

Definitions

Prior to discussing the present invention in further details, the following terms and conventions will first be defined:

The ligands (such as antibodies and antigen binding domains) of the invention bind selectively to MFAP4 that is they bind preferentially to MFAP4 with a greater binding affinity than to other antigens. The antibodies may bind selectively to human MFAP4, but also bind detectably to non-human MFAP4, such as murine MFAP4. Alternatively, the antibodies may bind exclusively to human MFAP4, with no detectable binding to non-human MFAP4.

The term "protein ligand" refers to ligands constituted mainly of amino acids, such as antibodies or fragments thereof. As also disclosed in here, the protein ligands may comprise moieties such as detectable labels or a substance having toxic or therapeutic activities.

The term "monoclonal antibody" refers to an antibody obtained from a population of substantially homogeneous antibodies, wherein each monoclonal antibody will typically recognize a single epitope on the antigen. The term "monoclonal" is not limited to any particular method for making the antibody. For example, monoclonal antibodies of the invention may be made by the hybridoma method as described in Kohler et al. Nature 256, 495 (1975) or may be isolated from phage libraries using the techniques as described herein.

The term "antigen binding domain" or "antigen binding region" or "fragment or derivative thereof" refers to that portion of the selective binding agent (such as an antibody molecule), which contains the amino acid residues that interact with an antigen and confer on the binding agent its specificity and affinity for the antigen. Preferably, the antigen binding region will be of human origin. In other embodiments, the antigen binding region can be derived from other animal species, in particular domestic animal and rodents such as rabbit, rat or hamster. The terms "effective amount" and "therapeutically effective amount" when used in relation to an antibody or antigen binding domain, fragment or derivative thereof, immunoreactive with a MFAP4 peptide, refer to an amount of a selective binding agent that is useful or necessary to support an observable change in the level of one or more biological activities of MFAP4, wherein said change may be either an increase or decrease in the level of MFAP4 activity.

In the context of the present invention, the term "sequence identity" or "homologue" indicates a quantitative measure of the degree of homology between two amino acid sequences or between two nucleic acid sequences. If the two sequences to be compared are not of equal length, they must be aligned to give the best possible fit, allowing the insertion of gaps or, alternatively, truncation at the ends of the polypeptide sequences or nucleotide sequences. The sequence identity can be calculated as $$\frac{(N_{ref} - N_{dif})100}{N_{ref}},$$

wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (Ndif=2 and Nref=8). A gap is counted as non-identity of the specific residue(s), i.e. the DNA sequence AGTGTC will have a sequence identity of 75% with the DNA sequence AGTCAGTC (Ndif=2 and Nref=8).

With respect to all embodiments of the invention relating to amino acid sequences or nucleotide sequences, the percentage of sequence identity between one or more sequences may also be based on alignments using the clustalW software (http:/www.ebi.ac.uk/clustalW/index.html) with default settings. For nucleotide sequence alignments these settings are: Alignment=3Dfull, Gap Open 10.00, Gap Ext. 0.20, Gap separation Dist. 4, DNA weight matrix: identity (IUB). For amino acid sequence alignments the settings are as follows: Alignment=3Dfull, Gap Open 10.00, Gap Ext. 0.20, Gap separation Dist. 4, Protein weight matrix: Gonnet.

Alternatively, nucleotide sequences may be analysed using programme DNASIS Max and the comparison of the sequences may be done at http://www.paralign.org/. This service is based on the two comparison algorithms called Smith-Waterman (SW) and ParAlign. The first algorithm was published by Smith and Waterman (1981) and is a well-established method that finds the optimal local alignment of two sequences. The other algorithm, ParAlign, is a heuristic method for sequence alignment; details on the method are published in Rognes (2001). Default settings for score matrix and Gap penalties as well as E-values were used.

In the present context, the terms "$K_D$" or "$K_D$ value" refer to the equilibrium dissociation constant between the antibody (ligand) and its antigen. The $K_D$ value relates to the concentration of antibody (the amount of antibody needed for a particular experiment) and so the lower the $K_D$ value (lower concentration) and thus the higher the affinity of the antibody. In the present context, $K_D$ is measured by Biacore T200.

In the context of the present invention, the definition "AA-yy referring to SEQ ID NO: X" is to be understood as AA=amino acid; -yy is the position of the amino acid in the SEQ ID NO: X. Thus, for example "Trp-33 referring to SEQ ID NO: 2" is to be understood as Trp at position 33 in SEQ ID NO: 2.

In the context of the present invention, the definition "at the most five amino acids" is to be understood as no more than five amino acids i.e. five amino acids, four amino acids, three amino acids, two amino acids or one amino acid.

In the context of the present invention, the definition "a sequence where at the most xx amino acids differ from the SEQ ID NO: X" is to be understood as the sequence being identical to the SEQ ID NO: X except for xx amino acids, which may be different i.e. a different amino acid than the one listed in the sequence. Thus, if at the most two amino acids differ from the SEQ ID NO: 9 this is to be understood as a sequence which differs from the SEQ ID NO: 9 by two, one or none amino acids. "X" is to be understood as any of the sequence listings SEQ ID NO: 1-14 as listed herein. Alternatively, "X" is to be understood as any of the sequence listings SEQ ID NO: 9, SEQ ID NO: 10, SEQ ID NO: 11, SEQ ID NO: 12, SEQ ID NO: 13, SEQ ID NO: 14. "xx" is to be understood as any of the numbers five, four, three, two or one.

Ligand

As mentioned above, in here is disclosed novel antibodies targeting MFAP4, including humanized antibodies. These antibodies have different sequences and different binding properties compared to known antibodies targeting MFAP4. Medical uses of the antibodies are described in the example section. Thus, in a first aspect, the invention relates to a protein ligand, such as an antibody, which binds to a novel epitope of MFAP4.

The present inventors have identified that the antibodies according to the invention have different CDR sequences compared to known anti-MFAP4 antibodies. Thus, in yet an aspect, the invention relates to a protein ligand, such as an antibody, or a ligand according to the invention, comprising
   a light chain variable region comprising a CDR 1 region according SEQ ID NO: 9, a CDR 2 region according to SEQ ID NO: 10 and a CDR 3 region according to SEQ ID NO: 11; and
   a heavy chain variable region comprising a CDR 1 region according SEQ ID NO: 12, a CDR 2 region according to SEQ ID NO: 13 and a CDR 3 region according to SEQ ID NO: 14.

By means of X-ray crystallography of the paratope of the antibody according to this invention and the epitope of MFAP4 and performed as known to the skilled person in the art, the present inventors have further identified amino acids in the CDRs of the light chain variable region and heavy chain variable region, which strongly interact with the epitope of MFAP4 and thus are important for the binding of the paratope of antibody with the epitope of MFAP4. Thus, in one embodiment, the invention relates to a protein ligand, such as an antibody, or a ligand according to the invention, comprising
   a light chain variable region comprising
      a CDR 1 region according to SEQ ID NO: 9 or according to a sequence where at the most five amino acids differ, such as at the most four amino acids differ, like at the most three amino acids differ, such as at the most two amino acids differ, like at the most one amino acid differ from SEQ ID NO: 9 with the proviso that the amino acid at position 9 is a Tyr;
      a CDR 2 region according to SEQ ID NO: 10 or according to a sequence where at the most five amino acids differ, such as at the most four amino acids differ, like at the most three amino acids differ, such as at the most two amino acids differ, like at the most one amino acid differ from SEQ ID NO: 10; and a CDR 3 region according to SEQ ID NO: 11 or according to a sequence where at the most five amino acids differ, such as at the most four amino acids differ, like at the most three amino acids differ, such as at the most two amino acids differ, like at the most one amino acid differ from SEQ ID NO: 11 with the proviso that the amino acid at position 6 is a Tyr; and a heavy chain variable region comprising a CDR 1 region according SEQ ID NO: 12 or according to a sequence where at the most five amino acids differ, such as at the most four amino acids differ, like at the most three amino acids differ, such as at the most two amino acids differ, like at the most one amino acid differ from SEQ ID NO: 12 with the proviso that the amino acid at position 3 is a Trp;

a CDR 2 region according to SEQ ID NO: 13 or according to a sequence where at the most five amino acids differ, such as at the most four amino acids differ, like at the most three amino acids differ, such as at the most two amino acids differ, like at the most one amino acid differ from SEQ ID NO: 13; and a CDR 3 region according to SEQ ID NO: 14 or according to a sequence where at the most five amino acids differ, such as at the most four amino acids differ, like at the most three amino acids differ, such as at the most two amino acids differ, like at the most one amino acid differ from SEQ ID NO: 14 with the proviso that the amino acid at position 1 is a Glu and the amino acid at position 9 is a Trp.

Also, by means of X-ray crystallography performed as known to the skilled person in the art, the present inventors have further identified amino acids in the CDRs of the heavy chain variable region, which are strongly involved in the packaging of the antibody. Thus, in a still further embodiment, the invention relates to a protein ligand, such as an antibody, or a ligand according to the invention, comprising a light chain variable region comprising a CDR 1 region according SEQ ID NO: 9 or according to a sequence where at the most five amino acids differ, such as at the most four amino acids differ, like at the most three amino acids differ, such as at the most two amino acids differ, like at the most one amino acid differ from SEQ ID NO: 9 with the proviso that the amino acid at position 9 is a Tyr;

a CDR 2 region according to SEQ ID NO: 10 or according to a sequence where at the most five amino acids differ, such as at the most four amino acids differ, like at the most three amino acids differ, such as at the most two amino acids differ, like at the most one amino acid differ from SEQ ID NO: 10; and a CDR 3 region according to SEQ ID NO: 11 or according to a sequence where at the most five amino acids differ, such as at the most four amino acids differ, like at the most three amino acids differ, such as at the most two amino acids differ, like at the most one amino acid differ from SEQ ID NO: 11 with the proviso that the amino acid at position 6 is a Tyr; and a heavy chain variable region comprising a CDR 1 region according to SEQ ID NO: 12 or according to a sequence where at the most five amino acids differ, such as at the most four amino acids differ, like at the most three amino acids differ, such as at the most two amino acids differ, like at the most one amino acid differ from SEQ ID NO: 12 with the proviso that the amino acid at position 3 is a Trp and the amino acid at position 2 is a Met;

a CDR 2 region according to SEQ ID NO: 13 or according to a sequence where at the most five amino acids differ, such as at the most four amino acids differ, like at the most three amino acids differ, such as at the most two amino acids differ, like at the most one amino acid differ from SEQ ID NO: 13 with the proviso that the amino acid at position 4 is a Pro; and a CDR 3 region according to SEQ ID NO: 14 or according to a sequence where at the most five amino acids differ, such as at the most four amino acids differ, like at the most three amino acids differ, such as at the most two amino acids differ, like at the most one amino acid differ from SEQ ID NO: 14 with the proviso that the amino acid at position 1 is a Glu and the amino acid at position 9 is a Trp.

Thus, according to the above embodiments, the CDR regions may differ from the sequences as defined by the SEQ ID NO: 9-14 except for the particular amino acids demonstrated to be important for the binding to the epitope (see example 12).

As shown in the example section, novel antibodies against MFAP4 have been produced (see examples 3 and 4+corresponding figures). These antibodies have different binding properties compared to other MFAP4 antibodies (see example 5). The antibodies show several advantages compared to other antibodies against MFAP4:

The humanized version may be more stable in solution, by showing less aggregation (see example 6 and example 10).

The antibodies show beneficial effects against e.g. pathological ocular angiogenesis, vascular leakage and inflammation (see examples 7-9)

The inventors have also identified the light chain and heavy chain of the ligands according to the invention. Thus, in an embodiment, the ligand comprises:

a light chain variable region comprising the amino acid sequence of SEQ ID NO: 1 or 3, or sequences having at least 80% sequence identity, such as at least 90% sequence identity, or such as at least 95% sequence identity to SEQ ID NO: 1 or 3.

a heavy chain variable region comprising the amino acid sequence of SEQ ID NO: 2 or 4, or sequences having at least 80% sequence identity, such as at least 90% sequence identity, or such as at least 95% sequence identity to SEQ ID NO: 2 or 4.

SEQ ID NO's: 1 and 2 are the light chain and heavy chain from mAS0326 whereas SEQ ID NO's: 3 and 4 are the light chain and heavy chain from hAS0326.

In a further embodiment, the ligand comprises a light chain variable region comprising the amino acid sequence of SEQ ID NO: 3; and a heavy chain variable region comprising the amino acid sequence of SEQ ID NO: 4.

Thus, in this embodiment, the ligand comprises the light chain and heavy chain from hAS0326.

In a further embodiment, the ligand comprises:

a light chain variable region comprising the amino acid sequence of SEQ ID NO: 1 or 3, or sequences having at least 80% sequence identity, such as at least at least 90% sequence identity, like at least 95% sequence identity, such as 98% sequence identity, or like 99% sequence identity to SEQ ID NO: 1 or 3 with the proviso that the amino acid at position 32 is a Tyr and the amino acid at position 94 is a Tyr;

a heavy chain variable region comprising the amino acid sequence of SEQ ID NO: 2 or 4, or sequences having at least 80% sequence identity, such as at least 90% sequence identity, like at least 95% sequence identity, such as at least 98% sequence identity or like 99% sequence identity to SEQ ID NO: 2 or 4 with the proviso that the amino acid at position 33 is a Trp, the amino acid at position 99 is a Glu and the amino acid at position 107 is a Trp.

In a further embodiment, the ligand comprises:

a light chain variable region comprising the amino acid sequence of SEQ ID NO: 1 or 3, or sequences having at least 80% sequence identity, such as at least at least 90% sequence identity, like at least 95% sequence identity, such as 98% sequence identity, or like 99% sequence identity to SEQ ID NO: 1 or 3 with the proviso that the amino acid at position 32 is a Tyr and the amino acid at position 94 is a Tyr;

a heavy chain variable region comprising the amino acid sequence of SEQ ID NO: 2 or 4, or sequences having at least 80% sequence identity, such as at least 90% sequence identity, like at least 95% sequence identity, such as at least 98% sequence identity or like 99% sequence identity to SEQ ID NO: 2 or 4 with the proviso that the amino acid at position 33 is a Trp, the amino acid at position 34 is a Met, the amino acid at position 53 is a Pro, the amino acid at position 99 is a Glu and the amino acid at position 107 is a Trp.

Thus, according to the above embodiments, the regions may differ from the sequences as described by SEQ ID NO: 1-4 by varying degrees of sequence identity except for the particular amino acids demonstrated to be important for the binding to the epitope (see example 12).

The ligand may be produced in different forms. Thus, in an embodiment, the ligand is selected from the group consisting of a polyclonal antibody, a monoclonal antibody, an antibody, wherein the heavy chain and the light chain are connected by a flexible linker, an Fv molecule, an antigen binding fragment, a Fab fragment, a F(ab')$_2$ molecule, a fully human antibody, a humanized antibody, and a chimeric antibody. In one embodiment, the ligand is a F(ab')$_2$ molecule. In yet a preferred embodiment, the ligand is selected from the group consisting of a monoclonal antibody, a Fab fragment and a humanized monoclonal antibody. In yet another preferred embodiment, the antibody is humanized and/or monoclonal, preferably a humanized monoclonal antibody.

It may also be advantageous to couple different moieties to the ligand according to the invention. Thus, in an embodiment, the ligand is coupled to a detectable label or a substance having toxic or therapeutic activity.

It is of course important that the ligand is able to bind to the target with a sufficient binding efficiency. Thus, in another embodiment, the ligand has $K_D$ value to rhMFAP4 below $1*10^{-7}$, such as below $1*10^{-8}$, or such as below $1*10^{-9}$ M, or such as in the range $1*10^{-7}$ to $1*10^{-12}$ M, or such as in the range $1*10^{-7}$ to $1*10^{-10}$ M. Example 2 shows $K_D$ values for antibodies according to the invention.

For ligands according to the invention to perform as medicaments, they have to be sufficiently soluble and not form aggregates, which may precipitate. Thus, in yet an embodiment, the ligand according to the invention is primarily in a monomeric form (measured in PBS, pH 7.4). "Primarily" is to be understood as at least 90% of the ligands are in monomeric form, such as at least 95%.

The binding specificity of the ligand according to the invention is different from other known antibodies binding to MFAP4. Thus, in yet another embodiment, the ligand does not bind (directly) to the RGD-integrin interaction sequence in rhMFAP4, but still block MFAP4-mediated activity suggested by steric hindrance of integrin ligation. Binding data for antibodies according to the invention are provided in example 5.

The RGD-integrin interaction domain is located in a short N-terminal region preceding the fibrinogen related domain (FReD) (position 26-28 (when including the signal peptide) and in position 6-8 (when the signal peptide is not included).

Vector

The ligands according to the invention may be expressed by one or more vectors. Thus, in an aspect the invention relates to a vector (or vectors) encoding the ligand according to the invention. It is to be understood that e.g. the light chain or heavy chain may be expressed from two different vectors. In an embodiment, the vector is a plasmid.

Cell

The vectors may be expressing the ligand in a cell. Thus, yet an aspect of the invention relates to a cell expressing the ligand according to the invention, and/or a cell comprising the vector according to the invention. In an embodiment, the cells are CHO cells.

Composition

The ligand according to the invention may of course be in a composition (such as a pharmaceutical composition). Thus, in a further aspect, the invention relates to a composition comprising the ligand according to the invention, and one or more physiologically acceptable carriers, excipients and/or diluents. In an embodiment, said composition comprising one or more stabilizing agents and/or one or more buffering agents. In yet an embodiment, the stabilizing agent is a surfactant.

In yet a further embodiment, the composition further comprises a VEGF-A (including spliceforms hereof) or VEGF-receptor (VEGFR1/VEGFR2) antagonists or anti-VEGF drug, such as an anti-VEGF antibody. As shown in the example section, in certain instances a beneficial effect is seen with such combination.

Medicament

The ligand and/or composition according to the invention may be used as a medicament. Thus, yet a further aspect of the invention relates to the ligand and/or composition according to the invention for use as a medicament.

In an embodiment, the ligand or the composition is for use in the prevention or treatment of vascular proliferative diseases and/or related disorders in a mammal. In a preferred embodiment, the mammal is a human.

In another embodiment, the vascular proliferative diseases and/or related disorders are caused by hyperplasia or remodeling in blood vessels.

In a further embodiment, the vascular proliferative diseases and/or related disorders are caused by pathological neovascularization or present with vascular leakage or inflammation or fibrosis and/or related disorders in a mammal.

In yet a further embodiment, the diseases and/or related disorders are bronchiolar hyperplasia or eosinophilic inflammation in allergic asthma.

In a further embodiment, the vascular proliferative diseases and/or related disorders is characterized by pathological neovascularization in the eye. In a related embodiment, the disorders characterized by pathological neovascularization in the eye is selected from the group consisting of age related macular degeneration (AMD), including geographic athropy and proliferative AMD, retinal vein occlusion, retinopathy, hypertensive retinopathy, vitreomacular traction, and diabetic retinopathy (DR), including proliferative DR and diabetic macular edema.

In an embodiment, the vascular proliferative diseases and/or related disorders are cancers or other malignancies. In a related embodiment, the cancer or malignancy is selected from the group consisting of glioblastoma, head, neck and lung cancer.

The ligand or composition may be administered by different routes. Thus, in an embodiment, said ligand or composition is administered intravenously, ocularly (to the eye) or subcutaneously.

Method of Prevention or Treatment of Vascular Proliferative Diseases

In yet another aspect, the invention relates to a method of prevention or treatment of vascular proliferative diseases and/or related disorders in a mammal, said method comprising administering the ligand or the composition according to the invention to a mammal (in need thereof). In a preferred embodiment, said mammal is a human.

In an embodiment, the method is for prevention or treatment of the vascular proliferative diseases and/or related disorders caused by pathological neovascularization.

In yet an embodiment, the method is for prevention or treatment of bronchiolar hyperplasia and eosinophilic inflammation in allergic asthma.

In another embodiment, the method is for prevention or treatment of disorders characterized by pathological neovascularization in the eye. In a related embodiment, the disorders characterized by pathological neovascularization in the eye is selected from the group consisting of age related macular degeneration (AMD), including geographic athropy and proliferative AMD, retinal vein occlusion, retinopathy, hypertensive retinopathy, vitreomacular traction, and diabetic retinopathy (DR), including proliferative DR and diabetic macular edema.

In an embodiment, the vascular proliferative diseases and/or related disorders are cancers or other malignancies. In a related embodiment, the cancer or malignancy is selected the group consisting of from glioblastoma, head, neck and lung cancer.

The ligand or composition may be administered by different routes. Thus, in an embodiment, said ligand or composition is administered intravenously, to the eye, ocularly or subcutaneously.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1—Materials and Methods

In this example the materials and methods used in the following examples are described Buffers Tris-buffered saline (TBS): 140 mM NaCl, 10 mM Tris-HCl, 0.02% (w/v) NaN2, pH 7.4; TBS/Tw: TBS containing 0.05% (v/v) Tween 20 (polyoxyethylene sorbitan monolaurate, MERCK-Schuchardt); phosphate-buffered saline (PBS): 137 mM NaCl, 3 mM KCl, 8 mM $Na_2HPO_4$, 1.5 mM $KH_2PO_4$, pH 7.4; substrate buffer: 35 mM citric acid, 67 mM $Na_2HPO_4$, pH 5.0.

Generation of Mouse Monoclonal Antibodies hrMFAP4 used for immunization was produced as previously described (Saakmose et al. PLoS One. 2013 Dec. 4; 8(12)).

Monoclonal antibodies with affinity for hrMFAP4 were produced using standard hybridoma technique and MFAP4 deficient mice.

This procedure resulted in a series of monoclonal antibodies including:

HG Hyb 7-1 murine monoclonal antibody raised against human recombinant MFAP4 (hrMFAP4) (described e.g. in WO 2016/008498)

HG Hyb 7-5 murine monoclonal antibody raised against human recombinant MFAP4 (hrMFAP4) (described e.g. in WO 2014/114298)

mAS0326 murine monoclonal antibody raised against human recombinant MFAP4 (hrMFAP4) and chosen antibody for humanization.

All antibodies were amino acid sequenced using standard techniques.

Antibody Humanization mAS0326 antibody was humanized by Genscript (www.Genscript.com), using proprietary technology. Variable domain sequences were blasted against human germline and several framework regions FR1, FR2, and FR3 were selected independently from human FRs, which share the highest identity with the mouse antibody. Selected FRs were assembled with mAS0326 CDRs using overlapping PCR and phage display library was constructed for expression of Fab fragments. High MFAP4 protein-binding phages were selected after three rounds of panning using Genscript's proprietary FASEBA screening methodology. Selected Fab genes were amplified from phage DNA. Genes encoding Fab were fused with genes encoding the appropriate constant regions of human IgG1 in order to generate whole IgG. hAS0326 was selected as the best recombinant human MFAP4 binder in this series using Biacore T200 and the resulting light chain and heavy chain constructs were cloned into the mammalian expression vectors pcDNA3.1 plus.

Expression of Humanized Antibody and Recombinant Forms of MFAP4

ExpiCHO-S cells were transfected with human MFAP4 expression plasmid (pcDNA 3.4-hMFAP4 TOPO® TA), mouse MFAP4 expression plasmid (pcDNA5/FRT/V5-His TOPO® TA), human MFAP4 RGD-AAA mutation (pcDNA 3.1 plus) and the hAS0326 light and heavy chain expression plasmids (pcDNA3.1 plus-hAS0326 light chain) and (pcDNA3.1 plus-hAS0326 heavy chain) using Expi-Fectamine according to the manufacturer's protocol (hAS0326 light chain and hAS0326 heavy chain were co-transfected in a molar 1:1 ratio). After adding Expi-Fectamine CHO Enhancer and ExpiCHO Feed, the cells were incubated at 37° C. in 8% $CO_2$ for 10 days with shaking.

Purification of Recombinant Forms of MFAP4

The recombinant MFAP4 proteins released into the medium of the ExpiCHO-S cells were purified were affinity purified as described by Lausen et al. (J Biol Chem (1999) 274(45):32234-40) followed by anion ion-exchange chromatography on a Resource Q column (GE Healthcare Life Sciences) on a Akta FPLC apparatus (Amersham Pharmacia Biotech). The purity of the proteins was tested by SDS-PAGE followed by Coomassie staining using SimplyBlue™ SafeStain (Invitrogen).

Purification of Antibodies

The antibodies were purified on an Akta FPLC apparatus (Amersham Pharmacia Biotech) using standard Protein G purification. The culture supernatant was applied to the column and the column was washed in PBS (0.5 M NaCl) and antibodies eluted by increasing the concentration of citric acid. Antibody containing fractions were neutralized immediately with $Na_2CO_3$ and pooled. The pool of purified antibody was dialysed against PBS.

Biotinylation

The antibodies were dialyzed against phosphate-buffered saline adjusted to pH 8.5 with 3% (w/v) $Na_2CO_3$ and biotin-N-hydroxysuccinimide ester (Sigma H-1759, 40 mg/ml in dimethyl sulfoxide) was added at 0.17 mg/mg protein. The mixture was incubated O.N at 4° C. and dialyzed against PBS.

Epitope Mapping of Antibodies by Competition ELISA 96-well plates (Nunc-MaxiSorp) were coated with 0.5 µg recombinant human MFAP4 in PBS O.N at 4° C. followed by washing and then blocking in TBS/Tw O.N at 4° C. Biotinylated Mab (0.5 µg/ml) and unlabeled MAbs (diluted 2-fold from 20 µg/ml to 156 ng/ml) were premixed in a separate microtiterplate in TBS/Tw and then added to the MFAP4 coated microtiter plate. The plates were following incubated for 2 hours at R.T. The plates were washed three times in TBS/Tw and incubated for 20 min with Strepavidin Horseradish Peroxidase (HRP) conjugate (Invitrogen) diluted 1:2000 in TBS/Tw. After three final washes, the amount of bound enzyme was estimated by adding o-phenylenediamine (OPD, 0.8 mg/ml, Kementec, Taastrup, Denmark) dissolved in substrate buffer (0.03% freshly prepared $H_2O_2$) and allowed to react for 15 minutes in the dark at RT. Colour development was stopped by the addition of 100 µl 1 M $H_2SO_4$, and the plates were read at $OD_{492}$ nm with $OD_{600}$ nm as reference.

Test of Antibody Binding to Recombinant Mouse MFAP4, Recombinant Human MFAP4 and Recombinant Human MFAP4 with RGD-Sequence Mutated to AAA-Sequence 96-well plates (Nunc-MaxiSorp) (Nunc™) were coated with 0.5 µg recombinant mouse MFAP4, recombinant human MFAP4 and recombinant human MFAP4 with the RGD-sequence mutated to AAA in PBS O.N at 4° C. Coating was followed by washing and then blocking in TBS/Tw O.N at 4° C. Blocking was followed by addition of biotinylated antibodies diluted 2-fold from an initial concentration of 100 ng/ml. The plates were then incubated for 2 hours at R.T. The plates were washed three times in TBS/Tw and incubated for 20 minutes with Strepavidin Horseradish Peroxidase (HRP) conjugate (Invitrogen) diluted 1:2000 in TBS/Tw. After final three washes, the amount of bound enzyme was estimated by adding OPD (0.8 mg/ml, Kementec, Taastrup, Denmark) dissolved in in substrate buffer (0.03% freshly prepared $H_2O_2$) and allowed to react for 15 minutes in the dark at RT. Colour development was stopped by the addition of 100 µl 1 M $H_2SO_4$, and the plates were read at $OD_{492}$ nm with $OD_{600}$ nm as reference.

Sandwich ELISA Assays

In Sandwich ELISA assays, various anti-MFAP4 antibodies were immobilized at 1 µg/ml in PBS in the wells of 96-well plates (Nunc-MaxiSorp) O.N at 4° C. Washed three times in TBS/Tw followed by blocking with TBS/Tw O.N at 4° C. The plates were incubated with twofold dilutions of serum from human, mouse and from MFAP4-deficient mouse from an initial 1:50 dilution O.N at 4° C. The plates were washed three times in TBS/Tw followed by incubation with biotinylated antibodies (0.5 µg/ml in TBS/Tw) for 2 h at R.T. The plates were then washed 3 times in TBS/Tw and incubated for 20 min with Strepavidin Horseradish Peroxidase (HRP) conjugate (Invitrogen) diluted 1:2000 in TBS/Tw. After final 3 washes, the amount of bound enzyme was estimated by adding OPD (0.8 mg/ml, Kementec, Taastrup, Denmark) dissolved in in substrate buffer (0.03% $H_2O_2$ added immediately before use) and allowed to react for 15 minutes in the dark at RT. Colour development was stopped by the addition of 100 µl 1 M $H_2SO_4$, and the plates were read at $OD_{492}$ nm with $OD_{600}$ nm as reference.

Concentrating Antibodies for Aggregation Studies

The Protein G purified antibodies were concentrated using Vivaspin 2 centrifugal concentrators (Viva products) followed by incubation at 4° C. for 2 hours before performing size exclusion chromatography. The purity of the concentrated antibodies was tested by SDS-PAGE followed by Coomassie staining using SimplyBlue™ SafeStain (Invitrogen). The antibody concentration was estimated using optical density determination (OD280).

Size Exclusion Chromatography

Size exclusion chromatography was performed using 50 µl of the concentrated antibodies. The antibody sample was applied to an analytical Superose 6 column connected to an Akta FPLC system (Amersham Pharmacia Biotech) using PBS, pH 7.4, containing and 0.05% emulphogene as eluant at a flow rate of 0.4 ml/min.

Animals Ethics

Mice and rats were treated in accordance with ARVO Statement for the Use of Animals in Ophthalmic and Vision Research, at the University of Nottingham Biological Services Unit, under a UK Home Office license.

Mouse Choroidal Neovascularization (CNV) Model

Female C57/BL6J mice were used for this study. Animals were anaesthetised with an intraperitoneal (IP) injection of 50 mg/kg Ketaset (ketamine hydrochloride, Zoetis), and recovered with 0.5 mg/kg Sedastop (Atipamezole hydrochloride, Animalcare), IP. Pupils were dilated with topical applications of 5% phenylephrine hydrochloride (Bausch & Lomb) and 0.8% tropicamide (Bausch & Lomb), and eyes were coated with Lubrithal (Dechra) to prevent dehydration.

Lesions were produced using a Meridian Merilas 532a Green Laser Photocoagulator to penetrate the Bruch's membrane at 4 points per eye, in both eyes. The presence of a sub-retinal bubble was used to determine the successful rupture of the Bruch's membrane. Laser settings were maintained at 450 mW for 130 ms for each photocoagulation lesion.

Mice received an intraocular injection of 1 µg m/hAS0326, 5 µg m/hAS0326, 1 µg mouse IgG (DAKO) or saline as control, or 1 µg anti-VEGF-A (Biolegend). Antibodies were diluted to 0.5 µg/µl (2.5 µg/µl for 5 µg injections) in sterile PBS and 2 µl administered with a 36 gauge Hamilton needle (World Precision Instruments) with fine forceps used to stabilize the eye. Antibodies were administered on day 0 (post lesion), and day 7.

To visualize the vasculature and lesion development in vivo (day 7 and day 14), 200 µl of 100 mg/ml sodium fluorescein (Sigma-Aldrich) in saline was injected IP and allowed to circulate before imaging with a Micron IV Retinal Imaging Microscope (Phoenix Research Labs). Development of cataracts meant that some eyes were excluded from the consecutive fundus flourescein angiography (FFA).

After animal termination and ocular dissection (day 14), choroids were flatmounted and blocked in serum (5% Goat Serum, 3% Triton X-100, 1% BSA) and stained with Isolectin-B4 (IB4) (Sigma Aldrich, biotin conjugated) 5 µg/ml and CD45 (Abcam) 5 µg/ml overnight at 4° C. Streptavidin conjugated Alexafluor 488 2 µg/ml and donkey anti-rabbit Alexafluor 555 4 µg/ml were used to detect IB4 and CD45 staining respectively. Coverslips were mounted with Fluoroshield with DAPI.

Images were obtained using a Leica TCS SPE confocal microscope, and all settings were maintained between images. Lesion and inflammatory cell areas in µm² were measured directly by Imaris (Bitplane, UK). Any lesions that had merged, or animals in which the contralateral eye had burns measuring greater than 2 standard deviations from the mean were excluded from analysis.

Rat Streptozotocin (STZ)-Induced Diabetes Model

To induce diabetes, male Norway Brown rats (250-300 g, Envigo, US) were given a single IP injection of streptozotocin (STZ, 50 mg/kg, Sigma-Aldrich). Control rats were injected with 300 µl saline IP. A third of an insulin pellet (LinShin) was implanted subcutaneously to maintain body weight over the following 4 weeks. On day 4 post-induction, blood was taken from the tail vein and blood glucose levels measured. Rats with blood glucose >15 mmol/l and were deemed diabetic. STZ-injected rats that did not become hyperglycaemic on day 4 were re-injected with STZ the following morning.

Rats were anaesthetized with 3-5% isoflurane (IsoFlo, Abbott Laboratories), pupils dilated with topical applications of 5% phenylephrine hydrochloride (Bausch & Lomb) and 0.8% tropicamide (Bausch & Lomb), and eyes were coated with Lubrithal (Dechra) to prevent dehydration. Animals received an introcular injection of 1 µg m/hAS0326, 5 µg m/hAS0326, saline as control, or 1 µg anti-VEGF-A (Biolegend). Antibodies were diluted to 0.5 µg/µl (2.5 µg/µl for 5 µg injections) in sterile PBS and 2 µl administered with a 36 gauge Hamilton needle (World Precision Instruments) with fine forceps used to stabilize the eye. Antibodies were administered on day 0 (pre diabetic), and day 7 (post diabetic). To visualize the vasculature and lesion development in vivo (day 0, 7, 14 and 21), 200 µl of 100 mg/ml sodium fluorescein (Sigma-Aldrich) in saline was injected IP and allowed to circulate before imaging with a Micron IV Retinal Imaging Microscope (Phoenix Research Labs). Development of cataracts meant that some eyes were excluded from the consecutive fundus flourescein angiography (FFA).

Evans Blue dye preparation, administration and the consecutive monitoring of ocular vascular permeability by dissolving is previously described in Ved N, Clin Sci (Lond) 2017.

Statistics

All statistics and graphs were produced in GraphPad Prism 6. Statistics shown are for comparison between treatment groups. Comparisons were performed using Kruskall-Wallis test and Dunn's multiple comparisons test. Significant differences were indicated on graphs as asterisks, where: * $p<0.05$;  $p<0.01$; * $p<0.001$; **** $p<0.0001$.

Example 2—$K_D$ Estimates for the Interaction Between hAS0326 and mAS0326 to rhMFAP4

Aim

To estimate $K_D$ values for the interaction between hAS0326 and mAS0326 to rhMFAP4.

Materials and Methods

Binding interactions between antibody of interest and rhMFAP4 was performed using Biacore T200 at GenScript.

Results

| Antibody | $K_D$ |
|---|---|
| hAS0326 | $1.14*10^{-9}$ M. |
| Chimeric antibody (mAS0326 with human Fc, CHO expression) | $5.04*10^{-10}$ M |
| mAS0326 | $1.4^{-10}$ M |

Conclusion

These results indicate that hAS0326 is a high-affinity antibody, with a $K_D$ in the nanomolar range. hAS0326 had lower rhMFAP4 affinity compared to mAS0326, but retained high affinity.

Example 3—Alignment of CDR Sequences in the Produced Monoclonal Antibodies

Figure 1:
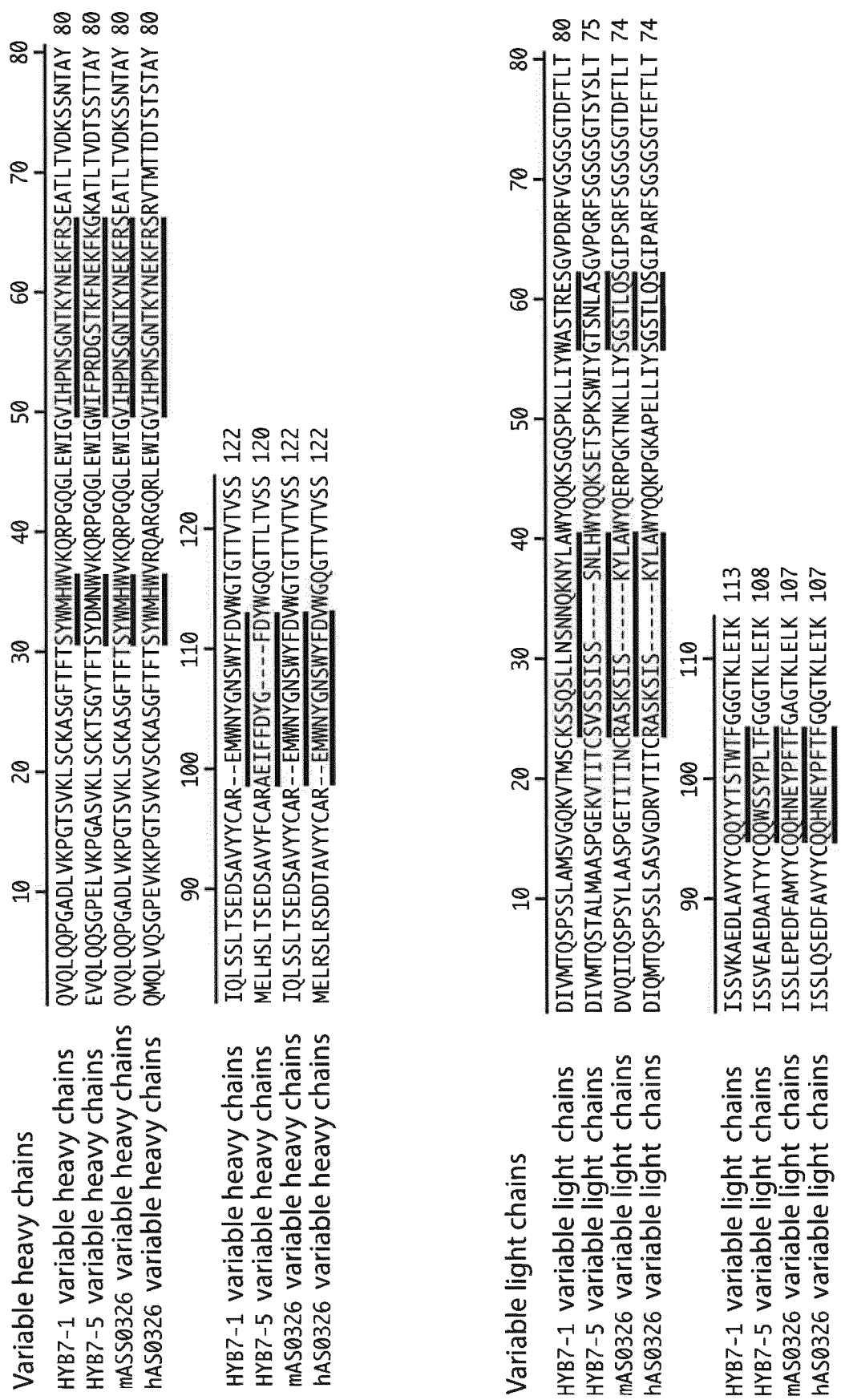
FIG. 1 shows alignment of variable heavy chain (HC) and light chain (LC) sequences for monoclonal antibodies HG Hyb 7-1 (HYB7-1)(LC=SEQ ID NO: 5 and HC=SEQ ID NO: 6), HG Hyb 7-5 (HYB7-5) (LC=SEQ ID NO: 7 and HC=SEQ ID NO: 8), mAS0326 (LC=SEQ ID NO: 1 and HC=SEQ ID NO: 2) and hAS0326 (LC=SEQ ID NO: 3 and HC=SEQ ID NO: 4). CDR sequences are indicated by underlining.

The CDR homologies between the produced antibodies HG Hyb 7-5, HG Hyb 7-1, mAS0326 and hAS0326 are depicted in FIG. 1.

100% homology between heavy chain CDR sequences for HG Hyb 7-1, mAS0326 and hAS0326.
<50% homology between HG Hyb 7-5 and hAS0326 heavy chain CDR.
100% homology between light chain CDR sequences for mAS0326 and hAS0326.
<50% homology between HG Hyb 7-1 or HG Hyb 7-5 and hAS0326 light chain CDR.

Example 4—Heavy and Light Chain Variable Domain Homologies Between Monoclonal Antibodies hAS0326 heavy chain variable domain has the following homologies to the produced mouse monoclonal antibodies
HG Hyb 7-1: 78.7%
HG Hyb 7-5: 66.1%
mAS0326: 78.7% hAS0326 light chain variable domain has the following homologies to the produced mouse monoclonal antibodies:
HG Hyb 7-1: 66.4%
HG Hyb 7-5: 61.7%
mAS0326: 79.4%

Conclusion

All homologies were <80%, which indicates that hAS0326 amino acid sequence is markedly dissimilar relative to the other tested antibodies, including antibodies presented in previous patent applications.

Example 5—MFAP4 Binding Properties of hAS0326/mAS0326 in Comparison to HG HYB7-5

Aim

To evaluate MFAP4 binding properties of hAS0326/mAS0326 in comparison to HG HYB7-5.

Results

Figure 2:
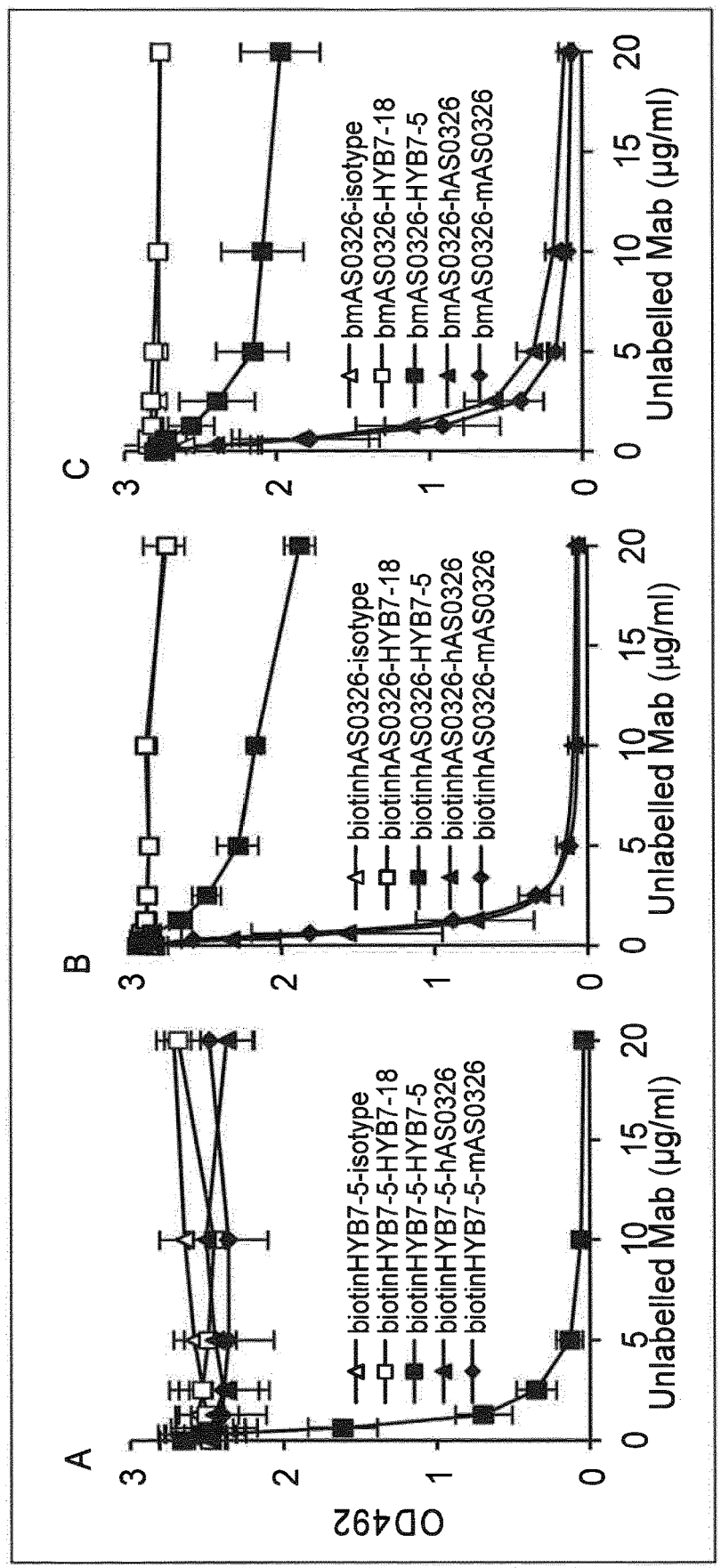
FIG. 2 shows epitope mapping of antibodies by competition ELISA. Biotinylated A) HG HYB 7-5 (biotinHYB7-5), B) hAS0326 (biotinhAS0426) and C) mAS0326 (bmAS0326) at a fixed concentration of 0.5 µg/ml were mixed with unlabelled IgG isotype control, HG HYB 7-18

It is demonstrated that HG HYB7-5 has a different epitope compared to hAS0326 and mAS0326 using a competitive ELISA setup (FIG. 2). In a direct binding assay using purified recombinant mouse MFAP4, recombinant human MFAP4 and recombinant human MFAP4 with the RGD integrin binding motif mutated to AAA it was demonstrated that the RGD motif is an essential part of the HG HYB7-5 epitope, whereas it is not a part of the hAS0326/mAS0326 epitope (FIGS. 3A and 3B). Furthermore it is demonstrated that whereas hAS0326/mAS0326 binds equally well to human and mouse MFAP4, HYB7-5 does not bind mouse MFAP4 (FIG. 3C).

Using serum as a source of native mouse and human MFAP4, FIG. 4 demonstrates that HG HYB 7-5 does not bind mouse MFAP4 whereas hAS0326/mAS0326 does.

Conclusion

Studies of sequence homology and epitope overlap revealed that HG Hyb 7-5 and mAS0326 (and hAS0236) had low CDR/variable chain homology and that they recognize different recombinant MFAP4 epitopes. Further, it is demonstrated that HG Hyb 7-5 recognizes the RGD-integrin interaction domain in rhMFAP4 whereas mAS0326 (and hAS0236) does not react with the RGD-integrin interaction domain in recombinant human MFAP4. Furthermore, it is demonstrated that AS0326 has interaction with murine MFAP4 whereas HG HYB 7-5 has not.

Example 6—Antibody Aggregation

Aim

To compare the aggregation properties of hAS0326 and mAS0326

Results

After concentrating antibody solutions, it was demonstrated that aggregation properties of hAS0326 and mAS0326 are different (FIG. 5). hAS0326 essentially stays in a monomeric form. In contrast, mAS0326 forms aggregates.

Conclusion hAS0326 was more stable in solution than mAS0326, which formed aggregates shortly after preparation and thus was not suitable for clinical use. The lack of aggregation of hAS0326 suggests that this antibody may be suitable for clinical use in the present form.

Example 7—Ability of mAS0326 to Reduce Ocular Angiogenesis, Vascular Leakage and Inflammation in the Mouse Laser-Induced Choroidal Neovascularization (CNV) Model of Wet Age-Induced Macular Degeneration (Wet AMD)

Aim

To evaluate the ability of mAS0326 to reduce ocular angiogenesis, vascular leakage or inflammation in the mouse laser-induced choroidal neovascularization (CNV) model of wet age-induced macular degeneration (wet AMD).

Results

Figures 6A, 6B:
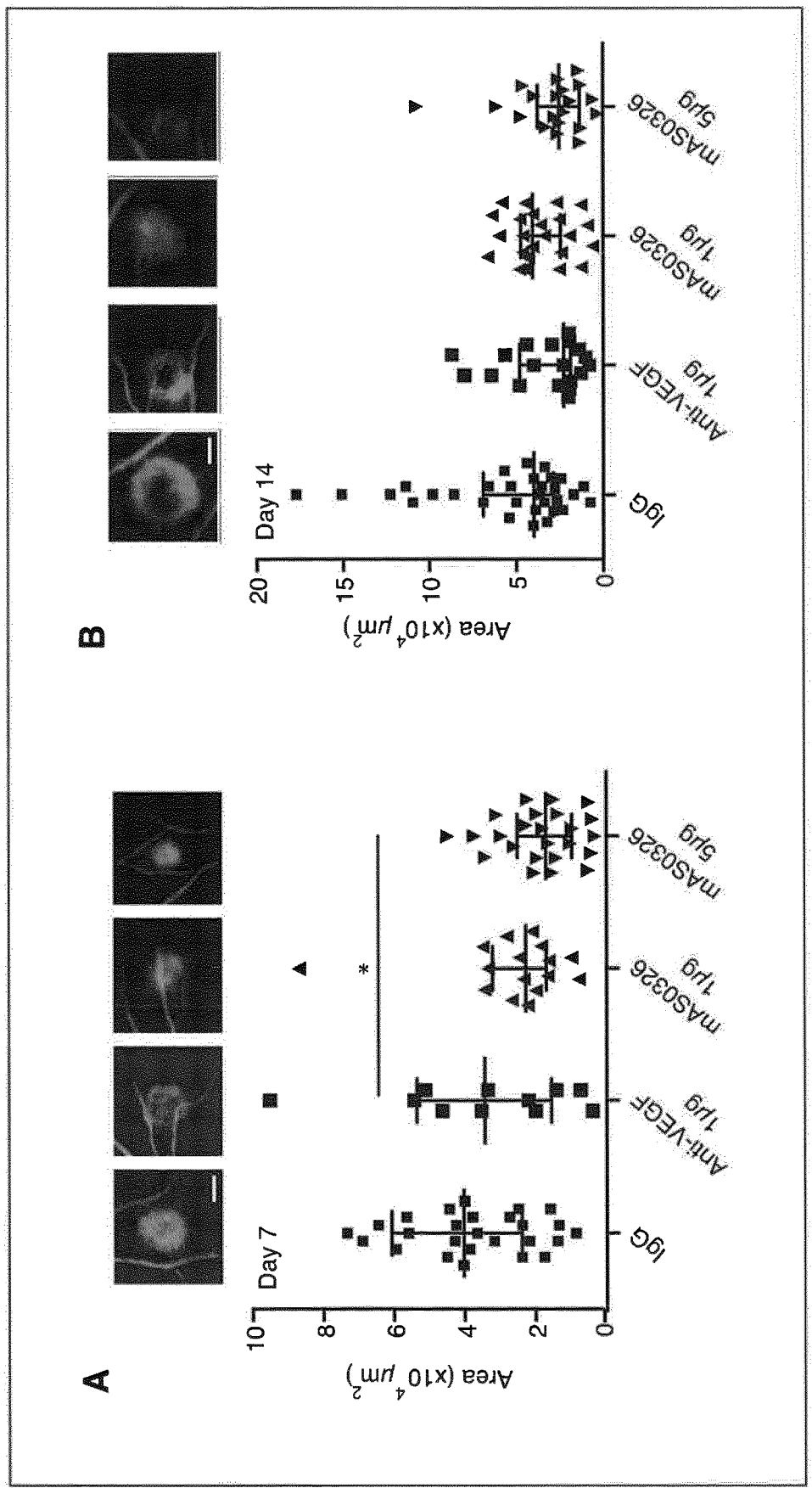
Figures 6C, 6D:
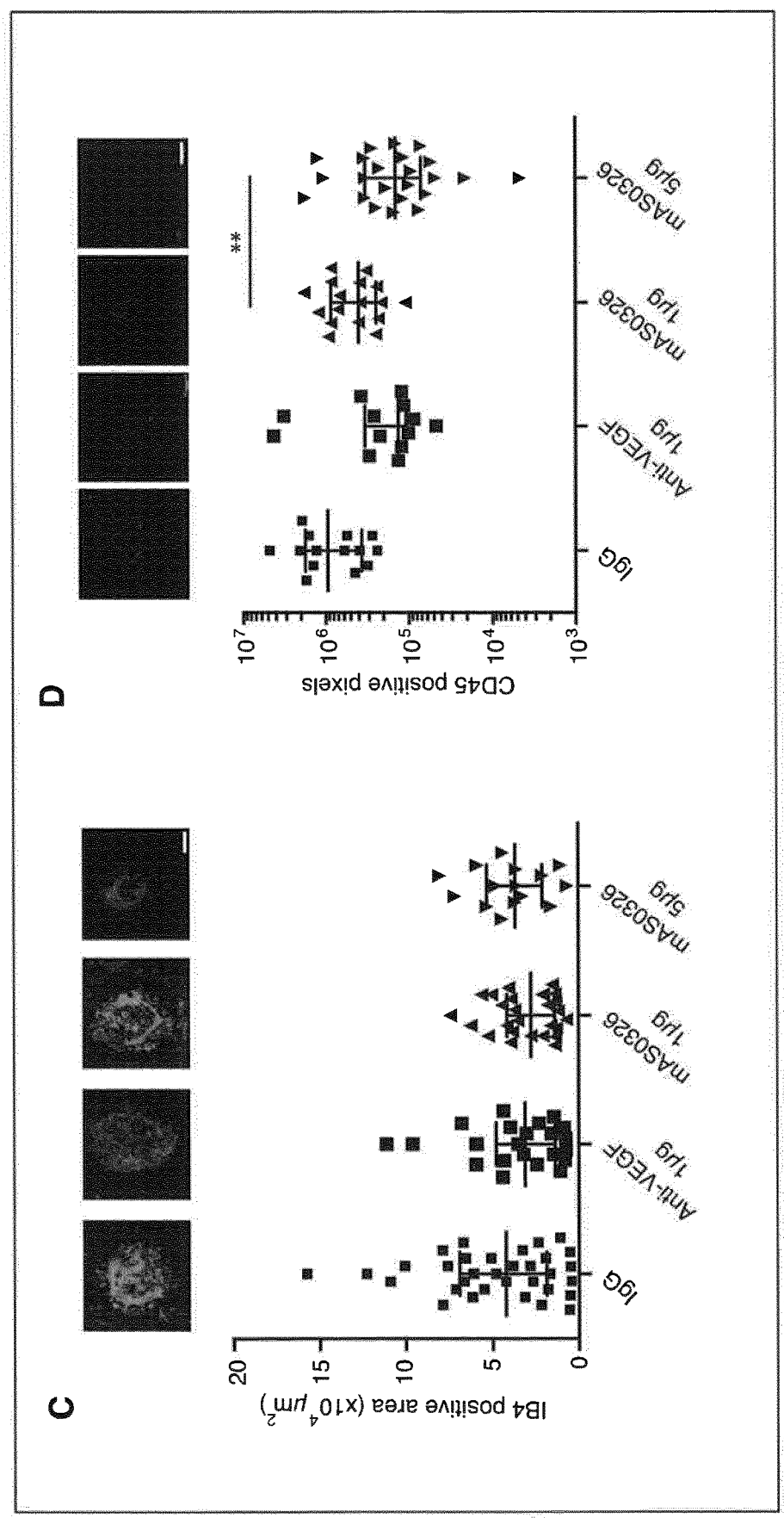

Seven and 14 days after laser-induced CNV, injection with sodium fluorescein highlighted the vasculature within the eye, and showed laser burns and regions of leakage. At day 7, there was no significant difference between the IgG negative control and the anti-VEGF positive control (FIG. 6A). Treatment with 5 µg mAS326 significantly reduced the lesion size compared to anti-VEGF positive control (P<0.05).

At day 14, further fluorescein angiograms were taken immediately before culling and tissue collection. As seen at day 7, 5 µg mAS0326 was able to significantly reduce lesion size compared to IgG controls (p<0.01, not shown in figure) (FIG. 6B). However, no significant differences were found between treatment groups.

Staining of vasculature with the endothelial marker IB4 showed no significant differences in burn area between any of the treatment groups (FIG. 6C) in line with observations in FIG. 6B.

Choroids were immunostained for CD45 expression to detect infiltration of inflammatory cells into the laser burn area (FIG. 6D). 1 µg anti-VEGF as well as 5 µg mAS0326 treatment both significantly reduced inflammatory cell infiltration relative to the IgG negative control (p<0.01 and p<0.0001, respectively, staistics not shown in figure). Moreover, 5 µg mAS0326 treatment significantly reduced inflammatory cell infiltration relative to the 1 µg anti-VEGF positive control (p<0.01).

Conclusion mAS0326 efficacy study in the mouse CNV for wet AMD showed proof-of-concept for beneficial effect against pathological ocular angiogenesis, vascular leakage and inflammation. The observed efficacy was similar and/or superior to the efficacy of standard treatment anti-VEGF.

Example 8—Ability of hAS0326 to Reduce Ocular Angiogenesis, Vascular Leakage and Inflammation in the Mouse Laser-Induced CNV Model of Wet AMD Aim To evaluate the Ability of hAS0326 to reduce ocular angiogenesis, vascular leakage or inflammation in the mouse laser-induced CNV model of wet AMD.

Results

Figures 7A, 7B:
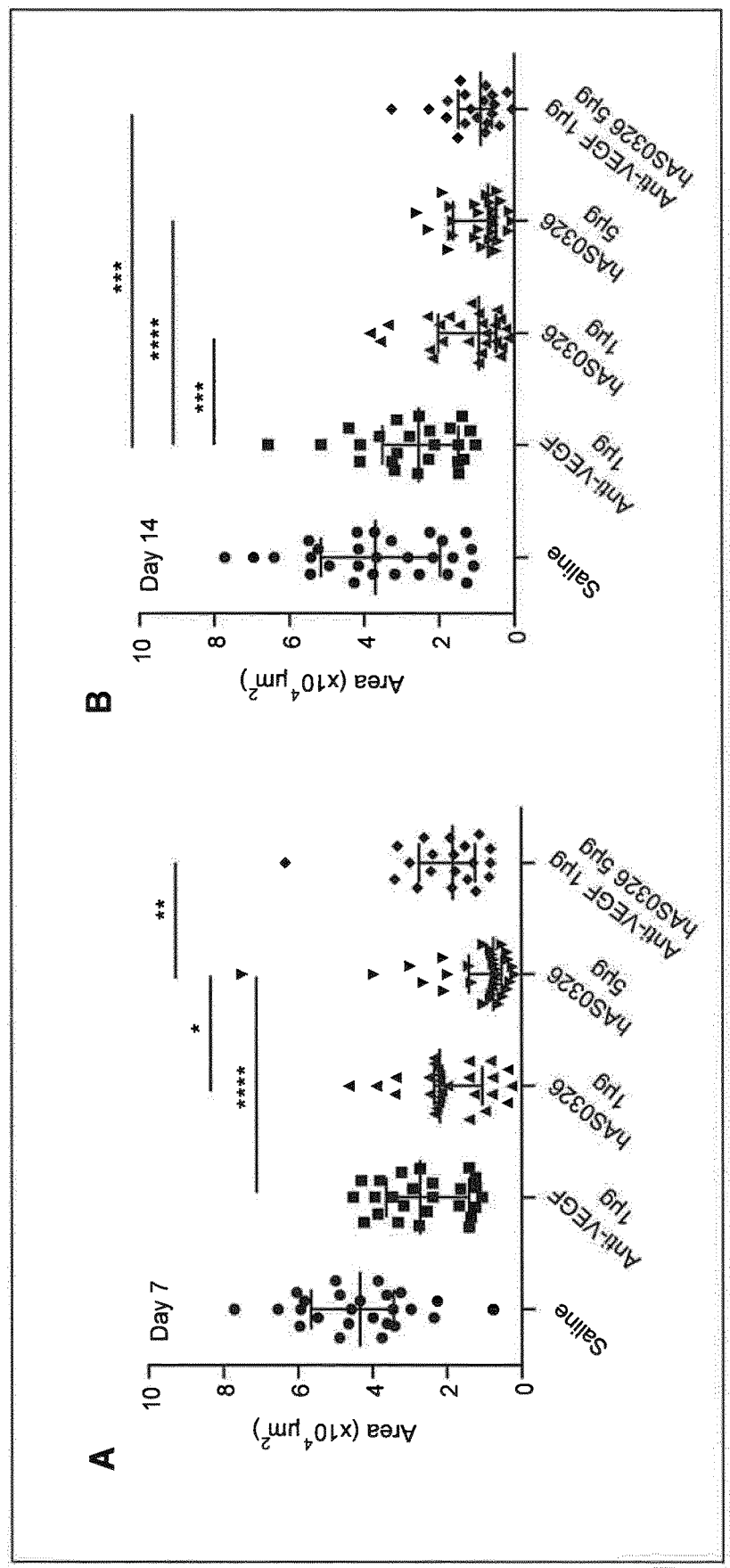

In contrast to the mAS0326 CNV trial described above (example 7), the separation from control treatments was clear in this hAS0326 CNV trial where saline was used as negative control. At day 7, all treatments provided significantly reduced lesions sizes compared to the saline negative control (p<0.0001-p<0.05 statistics not shown) (FIG. 7A). Treatment with 5 µg hAS326 significantly reduced the lesion size compared to anti-VEGF positive control (p<0.001 and <0.0001, respectively) (FIG. 7B). No significant differences in lesion size were found between hAS0326 treatment groups and there was no significant effect of combining hAS0326 and anti-VEGF treatment.

Figures 7C, 7D:
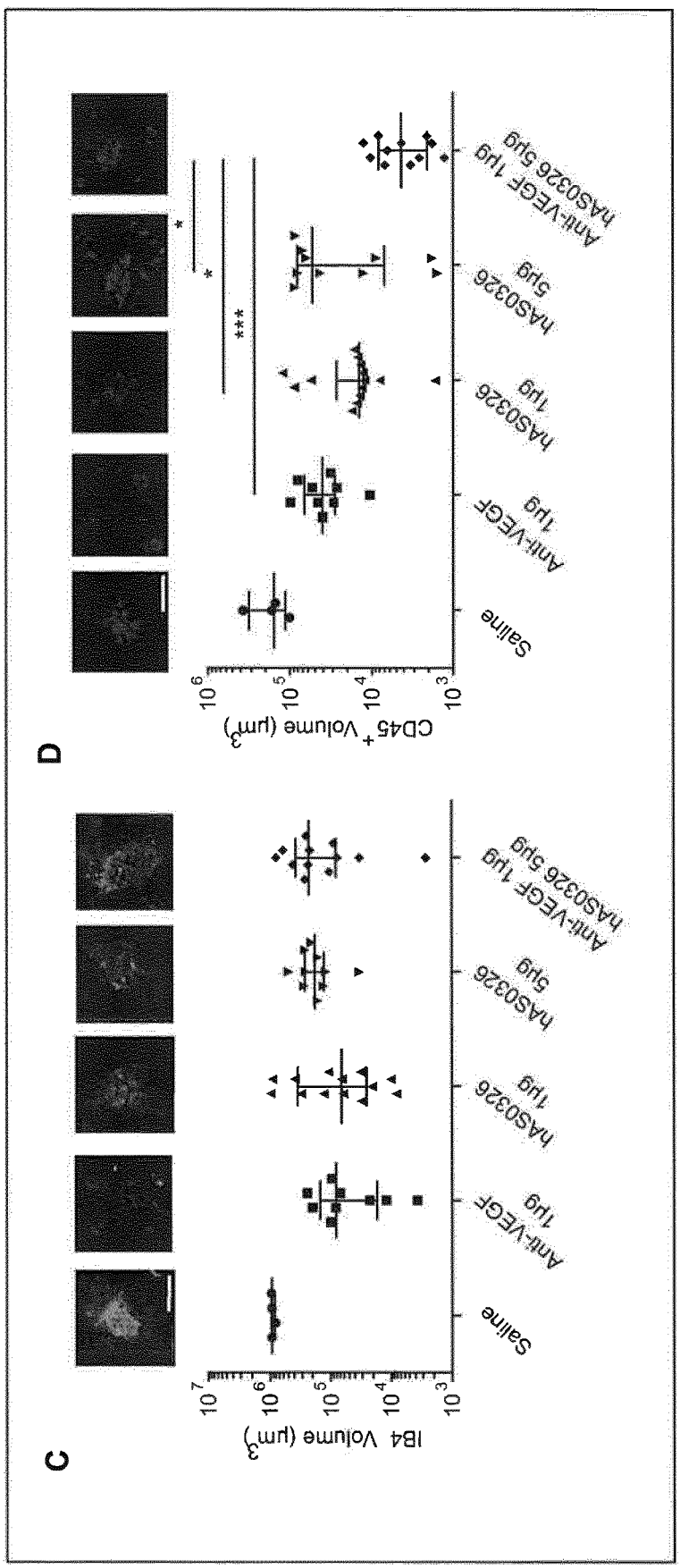

Staining of vasculature with the endothelial marker IB4 was significantly reduced by all treatments compared to saline control treatment (statistics not shown) (FIG. 7C). No significant differences in IB4 defined burn area were observed between any of the treatment groups (FIG. 7C).

Choroidal immunostaining for CD45 expression showed that all treatments significantly reduced inflammatory cell infiltration relative to the IgG negative control (statistics not shown in figure). The combinatorial treatment significantly reduced the inflammatory infiltration compared to all other treatment groups (FIG. 7D).

Conclusion hAS0326 efficacy study in the mouse CNV for wet AMD showed proof-of-concept for beneficial effect against pathological ocular angiogenesis, vascular leakage and inflammation. mAS0326 appeared with the same qualitative response as hAS0326. In contrast to hAS0326, the ability of mAS0326 treatment to reduce ocular lesion sizes in the CNV model were not significantly different from treatment with anti-VEGF. The observed hAS0326 efficacy was similar and/or superior to the efficacy of standard treatment anti-VEGF in the CNV model and combinatorial treatment with anti-VEGF and hAS0326 was superior to treatment with either compound alone in reduction of inflammation.

Example 9—Ability of hAS0326 to Reduce Ocular Angiogenesis in the Rat Streptozotocin (STZ)-Model of Diabetic Retinopathy Aim To evaluate the ability of hAS0326 to reduce ocular angiogenesis in the rat streptozotocin (STZ)-model of diabetic retinopathy.

Results

There was no statistical difference between the vascular areas in treatment groups before onset of STZ-model (FIG. 8A).

Twenty-one days after onset of STZ-treatment with induction of hyperglycemia (data not shown), treatment with 5 μg hAS0326 alone or combinatorial treatment with 1 μg anti-VEGF and 5 μg hAS0326 both significantly had reduced the lesion size compared to saline negative control ($p<0.001$ and $p<0.0001$, respectively, statistics not shown) (FIG. 8B). When comparing the efficacy of treatments, the combinatorial treatment with 1 μg anti-VEGF and 5 μg hAS0326 significantly reduced the lesion size compared to the anti-VEGF positive control ($p<0.05$) (FIG. 8B).

Conclusion hAS0326 efficacy study in reduction of vascular leakage in the rat streptozotocin (STZ)-model of diabetic retinopathy showed proof-of-concept for beneficial effect at par with anti-VEGF.

Example 10—Low pH and Thermal Stress Induces Aggregation of Monoclonal Antibodies HG HYB 7-5, HG HYB 7-14, mAS0326 and hAS0326 and Show Superior Stability of hAS0326

Aim

In order to evaluate and compare the stability of HG Hyb 7-5 (HYB7-5), HG Hyb 7-14 (HYB7-14), mAS0326 and hAS0326, we subjected the monoclonal antibodies (Mabs) to thermal stress. The formation of high molecular forms (aggregates) of the Mabs was induces by subjecting the Mabs to low pH and high temperatures and soluble aggregates were analyzed by size exclusion chromatography (SEC). The amounts of insoluble aggregates were tested using centrifugation followed by measurement of the protein concentration.

Material and Methods

Size Exclusion Chromatography

The HG Hyb 7-5, HG Hyb 7-14, mAS0326 and hAS0326 were purified using a 5 ml HiTrap column protein A (GE Healthcare) and following washed in 25 mM Tris, 25 mM NaCl pH 7.2 and then eluted in 100 mM citric acid pH 3.5. As a viral inactivation step the Mabs were incubated for 30 min in the elution buffer before adjustment to pH 5 using 1 M tris pH 8.6. After 5 and 10 days of incubation at 50° C. the samples were analyzed by size exclusion chromatography. 30 μl of the supernatant each stressed sample prepared at 6 mg/ml was injected onto a column (MabPac SEC-1 from Thermo Scientific) operated at 25° C., and the absorbance at 280 nm was recorded. The flow rate was 0.76 ml/min with a total elution time of 30 min. The mobile phase contained 50 mm sodium phosphate, pH 6.8, and 300 mm sodium chloride. High molecular weight (HMW) peaks included everything in the range between the excluded volume and the start of the anti-MFAP4 (monomer) peak. The integrated areas were taken as a percentage of the total integrated area.

Aggregate Concentration

To estimate the percent of original protein present as aggregates, stressed samples after 10 days at 50° C. were centrifuged at 12,000 rpm to pellet the insoluble material, and the protein concentration before and after centrifugation was determined by measuring the $A_{280}$ on a NanoDrop ONE UV-visible spectrophotometer (Thermo Scientific).

Results

Three high molecular weight forms of the Mabs were observed by SEC and their retention volumes are shown in Table 1 with reduced retention volumes compared to the monomeric Mab hAS0326. Thus, Table 1 shows an overview of high molecular weight (HMW) forms (aggregates) observed by size exclusion chromatography (MabPac SEC-1 column from Thermo Scientific) collectively for all experiments and with their respective retention volumes.

TABLE 1

| Type | Approximate volume (ml) |
|---|---|
| HMW1 | 6.1 |
| HMW2 | 7.7 |
| HMW3 | 8.1 |
| Anti-MFAP4 hAS0326 (monomer) | 10.1 |

HMW = High Molecular Weight: 1 HMW1 > HMW2 > HMV3 > anti-MFAP4 hAS0326 (monomer)

Low pH Stress Test

The Mabs were purified in parallel on a protein A column followed by a viral inactivation step at pH 3.5 for 30 min. Table 2 shows the distribution of the anti-MFAP4 Mabs High Molecular Weight (HMV) forms after the low pH viral inactivation step with only HG Hyb 7-14 and hAS0326 displaying a monodisperse distribution. Thus, Table 2 shows percentages of anti-MFAP4 and HMWs observed by size exclusion chromatography (soluble HMW forms) after protein A purification and viral inactivation for 30 min at pH 3.5.

TABLE 2

| Sample | % anti-MFAP4 (monomer) | % HMW1 | % HMW2 | % HMW3 |
|---|---|---|---|---|
| HG Hyb 7-5 | 97.7% | 0.0% | 0.0% | 2.3% |
| HG Hyb 7-14 | 100.0% | 0.0% | 0.0% | 0.0% |
| mAS0326 | 96.8% | 0.0% | 0.0% | 3.2% |
| hAS0326 | 100.0% | 0.0% | 0.0% | 0.0% |

Thermal Stress Test with to Time Intervals

Thermal stress tests of the Mabs were performed and the samples analyzed at day 5 and 10 using SEC in order to assess the amount of soluble HMW forms. As shown in Tables 3 and 4, hAS0326 displayed the lowest amount of HMW forms in both conditions. Thus, Table 3 shows percentages of anti-MFAP4 and HMW forms observed by size exclusion chromatography after thermal stress at 50 degrees Celcius for 5 days and Table 4 shows percentages of anti-MFAP4 and HMW forms observed by size exclusion chromatography after thermal stress at 50 degrees Celsius for 10 days.

TABLE 3

| Sample | % anti-MFAP4 (monomer) | % HMW1 | % HMW2 | % HMW3 |
|---|---|---|---|---|
| HG Hyb 7-5 | 91.0% | 7.2% | 0.0% | 1.8% |
| HG Hyb 7-14 | 96.6% | 3.4% | 0.0% | 0.0% |
| mAS0326 | 91.3% | 7.7% | 0.0% | 1.1% |
| hAS0326 | 99.4% | 0.0% | 0.0% | 0.6% |

TABLE 4

| Sample | % anti-MFAP4 (monomer) | % HMW1 | % HMW2 | % HMW3 |
|---|---|---|---|---|
| HG Hyb 7-5 | 84.6% | 13.8% | 0.0% | 1.6% |
| HG Hyb 7-14 | 90.8% | 8.9% | 0.0% | 0.3% |
| mAS0326 | 91.7% | 8.2% | 0.0% | 0.1% |
| hAS0326 | 96.4% | 0.0% | 2.5% | 2.1% |

To estimate the percentage of original protein present as insoluble aggregates, stressed samples (thermal stress at 50 degrees Celcius) were centrifuged at 12,000 rpm for 30 minutes to pellet the insoluble material, and the protein concentration before and after centrifugation was determined by measuring the A280 on a NanoDrop ONE (Thermo Scientific). The results obtained hereby is shown in Table 5 illustrating that unlike mAS0326 and HG Hyb 7-1, hAS0326 did not form any insoluble aggregates after 10 days at 50° C.

TABLE 5

| Sample | Before* | After** |
|---|---|---|
| HG Hyb 7-5 | 100% | 100% |
| HG Hyb 7-14 | 100% | 71% |
| mAS0326 | 100% | 51% |
| hAS0326 | 100% | 100% |

*Soluble protein before thermal stress
**Soluble protein after thermal stress (10 days)

Conclusion

The aggregate formation after low pH and thermal stress was markedly lower in hAS0326 compared to the mAS0326, HG Hyb 7-5 and HG Hyb 7-14 showing that the stability of hAS0326 was markedly higher.

Example 11—Inhibition of MFAP4-Induced Migration of Retinal Endothelial Cells—In Vitro Study Aim To study the effect of hAS0326 and variants thereof on blocking MFAP4-induced cellular activation, a retinal endothelial cell migration assay was performed. Full-length hAS0326, Fragment antigen-binding (Fab), and F(ab')$_2$ (including two Fabs) were tested.

Material and Methods

Expression of Full-Length Antibody and Antibody Variants

Full-length and antibody fragments were expressed in EXPI CHO cells (Thermo Scientific) as recommended by the manufacturer.

Endothelial Migration Assay

The experiment was performed using a modified Boyden migration assay and human retinal microvascular endothelial cells (Neuromics). The lower side of a 8 µm transwell filter (Falcon cat #35097) was coated with recombinant human MFAP4 10 µg/cm$^2$ overnight at 4° C. and following washed in PBS. 50.000 cells in 0.5 ml endothelial basal medium (PromoCell) with 0.5% FBS were added to the apical side of the filter and 1 ml endothelial basal medium with 0.5% FBS was added to the basal side of the filter. For inhibition of migration various Mabs and Mab variants were added together with VEGF (25 ng/ml) in the lower chamber. After 3.5 hours, the non-migrated cells were removed by swiping a cotton bud gently on the upper surface followed by wash in PBS and then the filter was stained with Reastain Quick-Diff kit (Gentaur Molecular Products). The cells that had traversed the membrane were counted under bright field microscopy (200× magnification).

Results

Full-length and antibody fragments were all able to inhibit endothelial migration but with a different efficiency. Full-length hAS0326 considerably inhibited endothelial migration whereas a recombinant Fab fragment of hAS0326 did not infer the same degree of inhibition even at increased doses (FIG. 9A).

The F(ab')$_2$ fragment of hAS0326 inhibited the migration to a similar degree as hAS0326 (FIG. 9B). It is considered well-established that if efficient F(ab)'s can be produced (which performs well in vitro compared to complete antibodies), they may very well perform better than complete antibodies in vivo, since the use of immunoglobulin fragments eliminate non-specific binding between the Fc portions of antibodies and the Fc receptor on cells. Thus, the production of an efficient F(ab')$_2$ fragment of hAS0326 makes it a promising candidate.

Conclusion

This in vitro assay demonstrates the ability of full-length hAS0326, hAS0326 Fab and hAS0326 F(ab')$_2$ to inhibit endothelial migration even though not at the same efficiency.

Example 12—X-Ray Crystallography of Interaction Between Epitope and Paratope Aim X-ray crystallography was used to determine the amino acids of the paratope important for the binding to the epitope of the MFAP4.

Materials and Methods

For Fab generation, anti-MFAP4 was incubated with immobilized papain beads (Thermo scientific) in 20 mM sodium phosphate, 10 mM EDTA and 20 mM L-cysteine pH 7.4 for 4 h at 37° C. Beads were pelleted by centrifugation and the supernatant was loaded on a 1 ml Mono S column equilibrated in 50 mM sodium acetate pH 5.5. The Fab was eluted with a gradient from 20 to 500 mM NaCl and subsequently purified by size exclusion chromatography on a 24 ml Superdex 200 increase equilibrated in 20 mM Hepes, 150 mM NaCl pH 7.4. Prior to crystallization MAP4 was deglycosylated for 18 hours at 4° C. with in house prepared Endoglycosidase H. Deglycosylated MFAP was mixed with an excess of Fab and the complex was purified on a 24 ml Superdex 200 Increase equilibrated in 20 mM Hepes pH 7.4, 150 mM NaCl. The isolated complex was concentrated to 6 mg/ml and crystallized by vapor diffusion at 19° C. after mixing 0.5 µl protein with 0.5 µl reservoir solution containing 0.14 M Ammonium phosphate dibasic, 14% w/v Polyethylene glycol 3,350. Prior to data collection crystals were soaked in reservoir solution supplemented with 20% glycerol and flash cooled in liquid nitrogen.

Diffraction data were collected at ESRF ID23-1 and processed and scaled with XDS and XSCALE (Kabsch, W.

(2010) *Acta crystallographica. Section D, Biological crystallography* 66, 133-144). The structure was determined by molecular replacement with Phaser (McCoy, A. J., Grosse-Kunstleve, R. W., Adams, P. D., Winn, M. D., Storoni, L. C., and Read, R. J. (2007) *Journal of applied crystallography* 40, 658-674) using the structure of monomeric FIBCD1 (PDB ID 4M7H) and a germline Fab (PDB ID 4JPI) as search models. In an iterative manner the structure was manually rebuilt in Coot and refined with Phenix.refine (Afonine, P. V. et al. (2012) *Acta Crystallogr D Biol Crystallogr* 68, 352-367) using positional refinement, grouped B-factors and TLS groups and positional non-crystallographic symmetry restraints. Upon completion of the protein part of the model the structure was fitted to the electron density map using molecular dynamics restrained real space fitting as described (Croll, T. I., et al. (2016) *Acta Crystallogr D Struct Biol* 72, 1006-1016). Subsequently $Ca^{2+}$ ions and two coordinating water molecules were inserted into each site, and the calcium-ligand coordination geometry was restrained according to that observed in FIBCD1 (Shrive, A. K. et al. (2014) *J Biol Chem* 289, 2880-2887). During the final refinement cycles a few cycle of individual B-factor refinement were allowed in addition to positional refinement. The final structure displayed excellent stereochemistry according to Molprobity (Chen, V. B. et al. (2010) *Acta Crystallogr D Biol Crystallogr* 66, 12-21) considering the resolution of the diffraction data. The intermolecular interface was analysed with PyMol 1.8.6 (Schrodinger, LLC. (2015) The PyMOL Molecular Graphics System, Version 1.8.) and PISA (Krissinel, E. et al. (2007) *J Mol Biol* 372, 774-797) and figures prepared in PyMol.

Results

The strongly interacting and packaging amino acids of the paratope comprises residues from all three CDRs in the variable heavy chain while only two CDRs of the variable light chain i.e. CDR1 and CDR3 show amino acids strongly interacting with the epitope in the MFAP4

The strongly interacting amino acids in the variable heavy chain are as follows:
In CDR1: Trp-33 referring to SEQ ID NO: 2 and 4; Trp-3 referring to SEQ ID NO: 12;
In CDR3: Glu-99 referring to SEQ ID NO: 2 and 4; Glu-1 referring to SEQ ID NO: 14;
In CDR3: Trp-107 referring to SEQ ID NO: 2 and 4; Trp-9 referring to SEQ ID NO: 14.

The strongly interacting amino acids in the variable light chain are as follows:
In CDR1: Tyr-32 referring to SEQ ID NO: 1 and 3; Tyr-9 referring to SEQ ID NO: 9;
In CDR3: Tyr-94 referring to SEQ ID NO: 1 and 3; Tyr-6 referring to SEQ ID NO:11.

The results further demonstrated that two amino acids in the variable heavy chain are important for packaging i.e. for correct folding of the paratope:
In CDR1: Met-34 referring to SEQ ID NO: 2 and 4; Met-4 referring to SEQ ID NO: 12;
In CDR2: Pro-53 referring to SEQ ID NO: 2 and 4; Pro-4 referring to SEQ ID NO: 13.

Conclusion

X-ray crystallography successfully defined the hAS0326 paratope and its binding to the MFAP4 epitope. The analysis shows that five amino acids of the paratope bind strongly to the epitope and that two amino acids are important for the packaging. Thus, it could be hypothesized that site directed mutagenesis of one or more of these amino acids may abolish or weaken the binding of the paratope to the epitope.

The invention claimed is:

1. A protein ligand, comprising:
   (a) a light chain variable region comprising the amino acid sequence of SEQ ID NO: 3, or a sequence having at least 90% sequence identity to SEQ ID NO: 3; and
   (b) a heavy chain variable region comprising the amino acid sequence of SEQ ID NO: 4, or a sequence having at least 90% sequence identity to SEQ ID NO: 4;
   the protein ligand comprising:
   (a) a light chain variable region comprising a CDR 1 region according to SEQ ID NO: 9, a CDR 2 region according to SEQ ID NO: 10, and a CDR 3 region according to SEQ ID NO: 11; and
   (b) a heavy chain variable region comprising a CDR 1 region according to SEQ ID NO: 12, a CDR 2 region according to SEQ ID NO: 13, and a CDR 3 region according to SEQ ID NO: 14.

2. The protein ligand according to claim 1, comprising:
   (a) a light chain variable region comprising the amino acid sequence of SEQ ID NO: 3; and
   (b) a heavy chain variable region comprising the amino acid sequence of SEQ ID NO: 4.

3. The protein ligand according to claim 1, wherein the ligand is selected from the group consisting of a polyclonal antibody, a monoclonal antibody, an antibody, wherein the heavy chain and the light chain are connected by a flexible linker, an Fv molecule, an antigen binding fragment, a Fab fragment, a Fab' fragment, a F(ab')2 molecule, a humanized antibody, and a chimeric antibody.

4. The protein ligand according to claim 1, wherein the ligand is a F(ab')2 molecule.

5. The protein ligand according to claim 1, wherein the antibody is humanized.

6. The protein ligand according to claim 1, wherein the antibody is a humanized monoclonal antibody.

7. The protein ligand according to claim 1, coupled to a detectable label or a substance having toxic or therapeutic activity.

8. The protein ligand according to claim 1, having KD value to rhMFAP4 below $1*10^{-7}$.

9. The protein ligand according to claim 1, being primarily in a monomeric form.

10. The protein ligand according to claim 1, wherein the ligand does not bind to the RGD-integrin interaction sequence in the rhMFAP4 N-terminal domain.

11. A vector encoding the ligand according to claim 1.

12. A cell expressing the ligand according to claim 1.

13. A cell comprising the vector according to claim 11.

14. A composition comprising the ligand according to claim 1, and one or more physiologically acceptable carriers, excipients and/or diluents.

15. A method of treating vascular proliferative diseases and/or related disorder in a mammal comprising administering the protein ligand according to claim 1 to a mammal in need of such treatment, wherein the vascular proliferative diseases and/or related disorder are characterized by pathological neovascularization, vascular leakage, inflammation, or fibrosis of the eye.

16. The method according to claim 15, wherein the disorder characterized by pathological neovascularization in the eye is selected from the group consisting of age related macular degeneration (AMD), including geographic athropy and proliferative AMD, retinal vein occlusion, retinopathy, hypertensive retinopathy, vitreomacular traction, and diabetic retinopathy (DR), including proliferative DR and diabetic macular edema.

17. The method according to claim 15, wherein the vascular proliferative diseases and/or related disorders are cancers or other malignancies.

* * * * *

SEQUENCE LISTING

```
<160> NUMBER OF SEQ ID NOS: 14

<210> SEQ ID NO 1
<211> LENGTH: 107
<212> TYPE: PRT
<213> ORGANISM: Artificial Sequence
<220> FEATURE:
<223> OTHER INFORMATION: Antibody sequences; mAS0326 variable light
      chain

<400> SEQUENCE: 1

Asp Val Gln Ile Ile Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Arg Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Phe
                85                  90                  95

Thr Phe Gly Ala Gly Thr Lys Leu Glu Leu Lys
            100                 105

<210> SEQ ID NO 2
```

```
<211> LENGTH: 122
<212> TYPE: PRT
<213> ORGANISM: Artificial Sequence
<220> FEATURE:
<223> OTHER INFORMATION: Antibody sequences; mAS0326 variable heavy
      chain

<400> SEQUENCE: 2

Gln Val Gln Leu Gln Gln Pro Gly Ala Asp Leu Val Lys Pro Gly Thr
1               5                   10                  15

Ser Val Lys Leu Ser Cys Lys Ala Ser Gly Phe Thr Phe Thr Ser Tyr
            20                  25                  30

Trp Met His Trp Val Lys Gln Arg Pro Gly Gln Gly Leu Glu Trp Ile
        35                  40                  45

Gly Val Ile His Pro Asn Ser Gly Asn Thr Lys Tyr Asn Glu Lys Phe
    50                  55                  60

Arg Ser Glu Ala Thr Leu Thr Val Asp Lys Ser Ser Asn Thr Ala Tyr
65                  70                  75                  80

Ile Gln Leu Ser Ser Leu Thr Ser Glu Asp Ser Ala Val Tyr Tyr Cys
                85                  90                  95

Ala Arg Glu Met Trp Asn Tyr Gly Asn Ser Trp Tyr Phe Asp Val Trp
            100                 105                 110

Gly Thr Gly Thr Thr Val Thr Val Ser Ser
        115                 120

<210> SEQ ID NO 3
<211> LENGTH: 107
<212> TYPE: PRT
<213> ORGANISM: Artificial Sequence
<220> FEATURE:
<223> OTHER INFORMATION: Antibody sequences; hAS0326 variable light
      chain

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Glu Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Asn Glu Tyr Pro Phe
                85                  90                  95

Thr Phe Gly Gln Gly Thr Lys Leu Glu Ile Lys
            100                 105

<210> SEQ ID NO 4
<211> LENGTH: 122
<212> TYPE: PRT
<213> ORGANISM: Artificial Sequence
<220> FEATURE:
<223> OTHER INFORMATION: Antibody sequences; hAS0326 variable heavy
      chain

<400> SEQUENCE: 4

Gln Met Gln Leu Val Gln Ser Gly Pro Glu Val Lys Lys Pro Gly Thr
1               5                   10                  15
```

```
Ser Val Lys Val Ser Cys Lys Ala Ser Gly Phe Thr Phe Thr Ser Tyr
            20                  25                  30

Trp Met His Trp Val Arg Gln Ala Arg Gly Gln Arg Leu Glu Trp Ile
        35                  40                  45

Gly Val Ile His Pro Asn Ser Gly Asn Thr Lys Tyr Asn Glu Lys Phe
    50                  55                  60

Arg Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Met Trp Asn Tyr Gly Asn Ser Trp Tyr Phe Asp Val Trp
            100                 105                 110

Gly Gln Gly Thr Thr Val Thr Val Ser Ser
            115                 120
```

<210> SEQ ID NO 5
<211> LENGTH: 113
<212> TYPE: PRT
<213> ORGANISM: Artificial Sequence
<220> FEATURE:
<223> OTHER INFORMATION: Antibody sequences; HYB7-1 variable light chain

<400> SEQUENCE: 5

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Asn Asn Gln Lys Asn Tyr Leu Ala Trp Tyr Gln Gln Lys Ser Gly Gln
        35                  40                  45

Ser Pro Lys Leu Leu Ile Tyr Trp Ala Ser Thr Arg Glu Ser Gly Val
    50                  55                  60

Pro Asp Arg Phe Val Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Thr Ser Thr Trp Thr Phe Gly Gly Gly Thr Lys Leu Glu Ile
            100                 105                 110

Lys
```

<210> SEQ ID NO 6
<211> LENGTH: 122
<212> TYPE: PRT
<213> ORGANISM: Artificial Sequence
<220> FEATURE:
<223> OTHER INFORMATION: Antibody sequences; HYB7-1 variable heavy chain

<400> SEQUENCE: 6

```
Gln Val Gln Leu Gln Gln Pro Gly Ala Asp Leu Val Lys Pro Gly Thr
1               5                   10                  15

Ser Val Lys Leu Ser Cys Lys Ala Ser Gly Phe Thr Phe Thr Ser Tyr
            20                  25                  30

Trp Met His Trp Val Lys Gln Arg Pro Gly Gln Gly Leu Glu Trp Ile
        35                  40                  45

Gly Val Ile His Pro Asn Ser Gly Asn Thr Lys Tyr Asn Glu Lys Phe
    50                  55                  60

Arg Ser Glu Ala Thr Leu Thr Val Asp Lys Ser Ser Asn Thr Ala Tyr
65                  70                  75                  80
```

```
Ile Gln Leu Ser Ser Leu Thr Ser Glu Asp Ser Ala Val Tyr Tyr Cys
                85                  90                  95

Ala Arg Glu Met Trp Asn Tyr Gly Asn Ser Trp Tyr Phe Asp Val Trp
            100                 105                 110

Gly Thr Gly Thr Thr Val Thr Val Ser Ser
        115                 120

<210> SEQ ID NO 7
<211> LENGTH: 108
<212> TYPE: PRT
<213> ORGANISM: Artificial Sequence
<220> FEATURE:
<223> OTHER INFORMATION: Antibody sequences; HYB7-5 variable light chain

<400> SEQUENCE: 7

Asp Ile Val Met Thr Gln Ser Thr Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Tyr Gln Gln Lys Ser Glu Thr Ser Pro Lys Ser Trp
        35                  40                  45

Ile Tyr Gly Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Trp Ser Ser Tyr Pro
                85                  90                  95

Leu Thr Phe Gly Gly Gly Thr Lys Leu Glu Ile Lys
            100                 105

<210> SEQ ID NO 8
<211> LENGTH: 120
<212> TYPE: PRT
<213> ORGANISM: Artificial Sequence
<220> FEATURE:
<223> OTHER INFORMATION: Antibody sequences; HYB7-5 variable heavy chain

<400> SEQUENCE: 8

Glu Val Gln Leu Gln Gln Ser Gly Pro Glu Leu Val Lys Pro Gly Ala
1               5                   10                  15

Ser Val Lys Leu Ser Cys Lys Thr Ser Gly Tyr Thr Phe Thr Ser Tyr
            20                  25                  30

Asp Met Asn Trp Val Lys Gln Arg Pro Gly Gln Gly Leu Glu Trp Ile
        35                  40                  45

Gly Trp Ile Phe Pro Arg Asp Gly Ser Thr Lys Phe Asn Glu Lys Phe
    50                  55                  60

Lys Gly Lys Ala Thr Leu Thr Val Asp Thr Ser Ser Thr Thr Ala Tyr
65                  70                  75                  80

Met Glu Leu His Ser Leu Thr Ser Glu Asp Ser Ala Val Tyr Phe Cys
                85                  90                  95

Ala Arg Ala Glu Ile Phe Phe Asp Tyr Gly Phe Asp Tyr Trp Gly Gln
            100                 105                 110

Gly Thr Thr Leu Thr Val Ser Ser
        115                 120

<210> SEQ ID NO 9
<211> LENGTH: 11
<212> TYPE: PRT
<213> ORGANISM: Artificial Sequence
```

```
<220> FEATURE:
<223> OTHER INFORMATION: Antibody sequences; light chain CDR1 region

<400> SEQUENCE: 9

Arg Ala Ser Lys Ser Ile Ser Lys Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Antibody sequences; light chain CDR2 region

<400> SEQUENCE: 10

Ser Gly Ser Thr Leu Gln Ser
1               5

<210> SEQ ID NO 11
<211> LENGTH: 10
<212> TYPE: PRT
<213> ORGANISM: Artificial Sequence
<220> FEATURE:
<223> OTHER INFORMATION: Antibody sequences; light chain CDR3 region

<400> SEQUENCE: 11

Gln Gln His Asn Glu Tyr Pro Phe Thr Phe
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Antibody sequences; heavy chain CDR1 region

<400> SEQUENCE: 12

Ser Tyr Trp Met His Trp
1               5

<210> SEQ ID NO 13
<211> LENGTH: 17
<212> TYPE: PRT
<213> ORGANISM: Artificial Sequence
<220> FEATURE:
<223> OTHER INFORMATION: Antibody sequences; heavy chain CDR2 region

<400> SEQUENCE: 13

Val Ile His Pro Asn Ser Gly Asn Thr Lys Tyr Asn Glu Lys Phe Arg
1               5                   10                  15

Ser

<210> SEQ ID NO 14
<211> LENGTH: 13
<212> TYPE: PRT
<213> ORGANISM: Artificial Sequence
<220> FEATURE:
<223> OTHER INFORMATION: Antibody sequences; heavy chain CDR3 region

<400> SEQUENCE: 14

Glu Met Trp Asn Tyr Gly Asn Ser Trp Tyr Phe Asp Val
1               5                   10
```